(12) United States Patent
Cunningham et al.

(10) Patent No.: US 8,268,637 B2
(45) Date of Patent: Sep. 18, 2012

(54) LABEL-FREE BIOSENSORS BASED UPON DISTRIBUTED FEEDBACK LASER

(75) Inventors: Brian T. Cunningham, Champaign, IL (US); Meng Lu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 771 days.

(21) Appl. No.: 12/317,826

(22) Filed: Dec. 29, 2008

(65) Prior Publication Data

US 2009/0179637 A1    Jul. 16, 2009

Related U.S. Application Data

(60) Provisional application No. 61/010,847, filed on Jan. 11, 2008.

(51) Int. Cl.
*G01N 33/551* (2006.01)

(52) U.S. Cl. ......... 436/524; 422/82.11; 435/5; 435/6.1; 435/7.32; 435/287.2; 435/288.7; 435/808; 436/164; 436/512; 436/525; 436/805

(58) Field of Classification Search .................. None
See application file for complete search history.

(56) References Cited

U.S. PATENT DOCUMENTS

| | | | |
|---|---|---|---|
| 5,216,680 A | 6/1993 | Magnusson et al. | 372/20 |
| 7,070,987 B2 | 7/2006 | Cunningham et al. | 435/289.5 |
| 7,162,125 B1 | 1/2007 | Schulz | 385/37 |
| 7,167,615 B1 | 1/2007 | Wawro et al. | 385/37 |
| 7,262,856 B2 | 8/2007 | Hobbs et al. | 456/436 |
| 7,310,153 B2 | 12/2007 | Kiesel et al. | 356/519 |
| 7,400,399 B2 | 7/2008 | Wawro et al. | 356/328 |
| 2003/0027327 A1 | 2/2003 | Cunningham et al. | 435/287.2 |
| 2004/0130761 A1 | 7/2004 | Moon et al. | 359/2 |
| 2005/0051635 A1* | 3/2005 | Attenberger et al. | 235/491 |

OTHER PUBLICATIONS

International Search Report and Written Opinion mailed Feb. 23, 2009, in PCT/US09/00073, filed Jan. 7, 2009.
International Preliminary Report on Patentability mailed Jul. 22, 2010 in PCT/US2009/000073, filed Jan. 7, 2009.
Narayanaswamy, R. & Wolfbeis, 0. ,*Optical Sensors: Industrial Environmental and Diagnostic Application*, Published by Springer-Verlag Berlin Heidelberg New York , Chapter 7, pp. 145-171 (2004).
Cunningham, B. et al., *A plastic colorimetric resonant optical biosensor for multiparallel detection of label-free biochemical interactions*, Sensors and Actuators B, vol. 85, pp. 219-226 (2002).
Cunningham, B.T. et al., *Label-free assays on the BIND system*, Journal of Biomolecular Screening, vol. 9, pp. 481-490 (2004).
Homola, J. et al., Surface *plasmon resonance sensors: review.*, Sensors and Actuators B, vol. 54, pp. 3-15 (1999).

(Continued)

*Primary Examiner* — Chris L Chin
(74) *Attorney, Agent, or Firm* — McDonnell Boehnen Hulbert & Berghoff LLP

(57) ABSTRACT

A biosensor based upon a vertically emitting, distributed feedback (DFB) laser is disclosed. In one configuration, the DFB laser comprises a replica-molded, one- or two-dimensional dielectric grating coated with a laser dye-doped-polymer as the gain medium. A sensor is also described in which the grating layer and the active layer are combined into a single layer. DFB lasers using an inorganic or organic thin film with alternating regions of high and low index of refraction as the active layer are also disclosed. The sensor actively generates its own narrowband high intensity light output without stringent requirements for coupling alignment, thereby resulting in a simple, robust illumination and detection configuration.

38 Claims, 12 Drawing Sheets

OTHER PUBLICATIONS

Armani, A.M. et al., *Label-free, single-molecule detection with optical microcavities.* Science, vol. 317, pp. 783-787 (2007).

Armani, A.M. et al., *Biological and chemical detection using ultra-high-Q toroidal microresonators*, International Society for Optical Engineering, SPIE Newsroom, pp. 1-2 (2006).

Stewart, M.E. et al. *Quantitative multispectral biosensing and 1D imaging using quasi-3D plasmonic crystals*, Proceedings of the National Academy of Sciences, vol. 103, pp. 17143-17148 (2006).

Tazawa, H., et al., *Fiber-optic coupler based refractive index sensor and its application to biosensing*, Applied Physics Letters, vol. 91, pp. 11309-1-11309-3 (2007).

Choi, C.J. & Cunningham, B.T., *A 96-well Microplate Incorporating a Replica Molded Microfluidic Network Integrated with Photonic Crystal Biosensors for High Throughput Kinetic Biomolecular Interaction Analysis*, Lab on a Chip, vol. 7, pp. 550-556 (2007).

Zhang, Y., et al., *Microgap multicavity Fabry-Pérot biosensor*, Journal of Lightwave Technology, vol. 25, pp. 1797-1804 (2007).

Chao, et al., *Polymer microring resonators for biochemical sensing applications*, IEEE Journal of Selected Topics in Quantum Electronics, vol. 12, No. 1, pp. 134-142 (2006).

Ganesh, N. et al., *Compact wavelength detection system incorporating a guided-mode resonance filter*, Applied Physics Letters, vol. 90, pp. 081103-1-081103-3 (2007).

Hill, K. O. et al., *Fiber Bragg Grating Technology Fundamentals and Overview*, Journal of Lightwave Technology, vol. 15, No. 8, pp. 1263-1276 (1997).

Starodubov, D. S., et al., *Efficient Bragg Grating Fabrication in a Fibre Through Its Polymer Jacket Using Near-UV Light*, Electronics Letters, vol. 33, pp. 1331-1333 (1997).

Starodubov, D. S., et al., *Bragg Grating Fabrication in Germanosilicate Fibers by Use of Near-UV Light: A New Pathway for Refractive-index Changes*, Optics Letters, vol. 22, No. 14, pp. 1086-1088 (1997).

Toccafondo, V., et al., *$Er^3$-doped $BaY_2F_8$ Crystal Waveguides for Broadband optical Amplification at 1.5 µm*, Journal of Applied Physics, vol. 101, pp. 023104-1-023104-6 (2007).

Yang, L., et al., *Erbium-doped and Raman Microlasers on a Silicon Chip Fabricated by the Sol-gel Process*, Applied Physics Letters, vol. 86, pp. 091114-1-091114-6 (2005).

Wang, X. J., et al., Preparation *and Photoluminescence of $Er^{3+}$-doped $Al_2O_3$ Films*, Thin Solid Films, vol. 476, pp. 41-45 (2005).

Kiesel, P., et al. Compact, *Low-cost, and High-resolution Interrogation. Unit for Optical Sensors*, Applied Physics.Letters, vol. 89, pp. 201113-1-201113-3 (2006).

Wawro et al., *Optical Fiber Endface Biosensor Based on Resonances in Dielectric Waveguide Gratings*, International Biomedical Optics Symposium Jan. 2000, Proceedings SPIE, vol. 3911, pp. 86-94 (2000).

\* cited by examiner

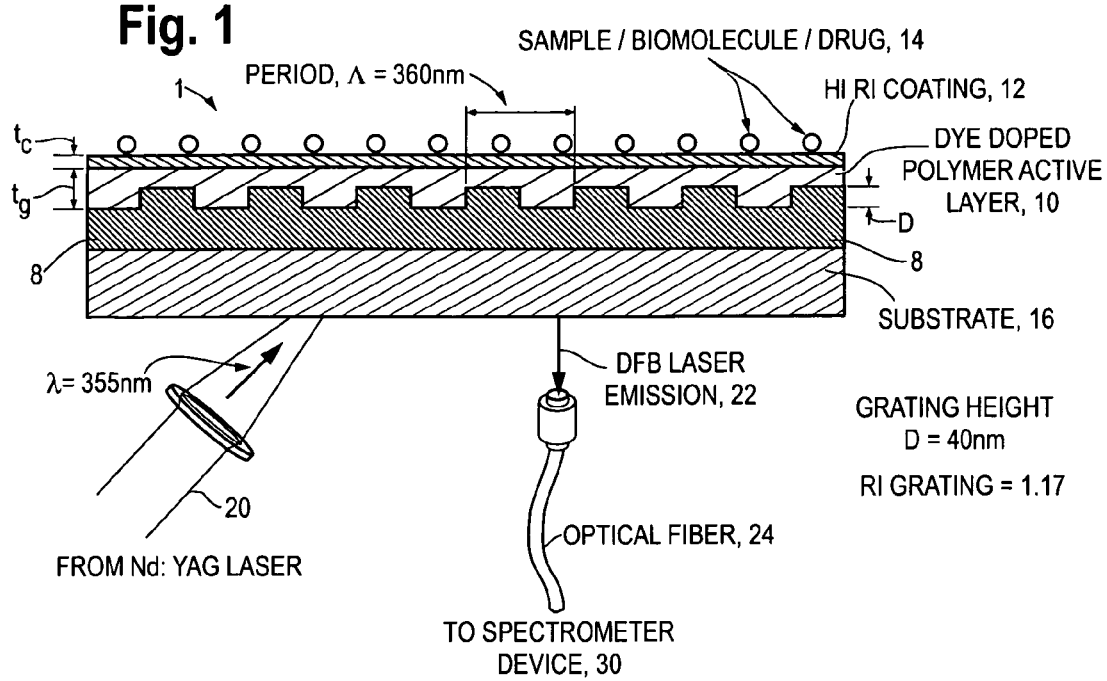
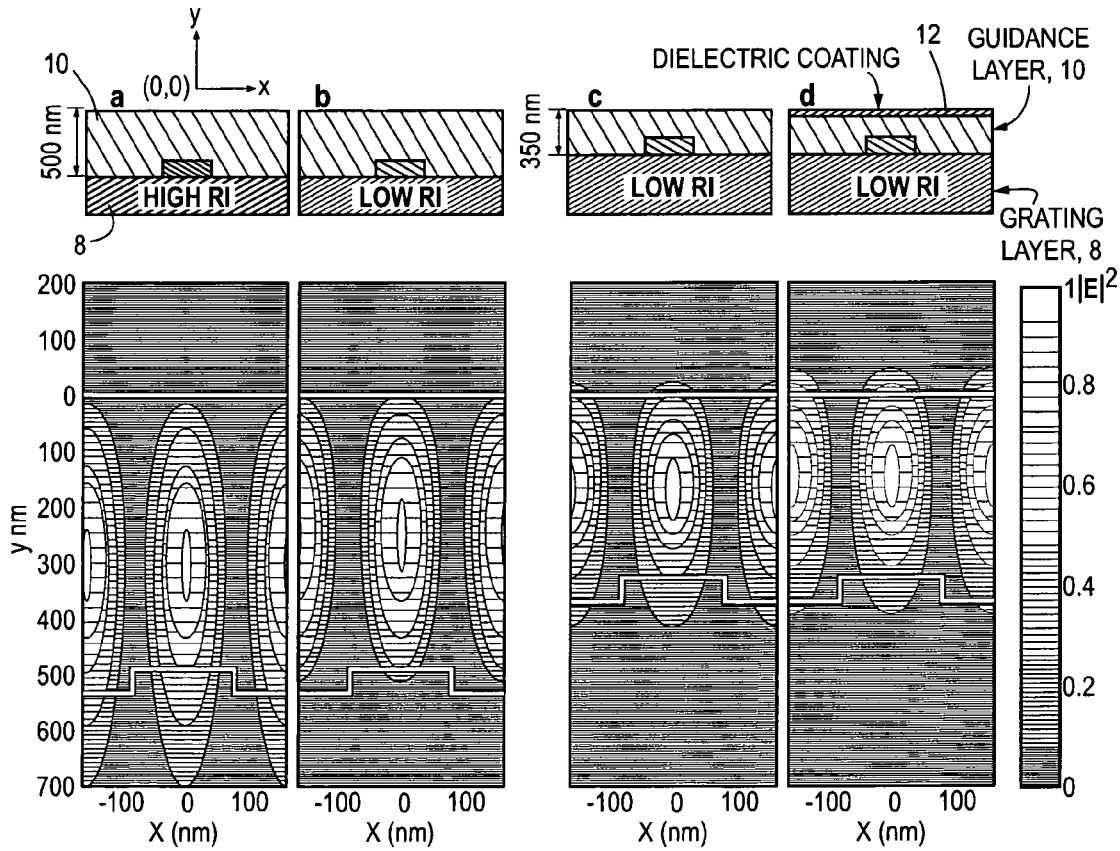

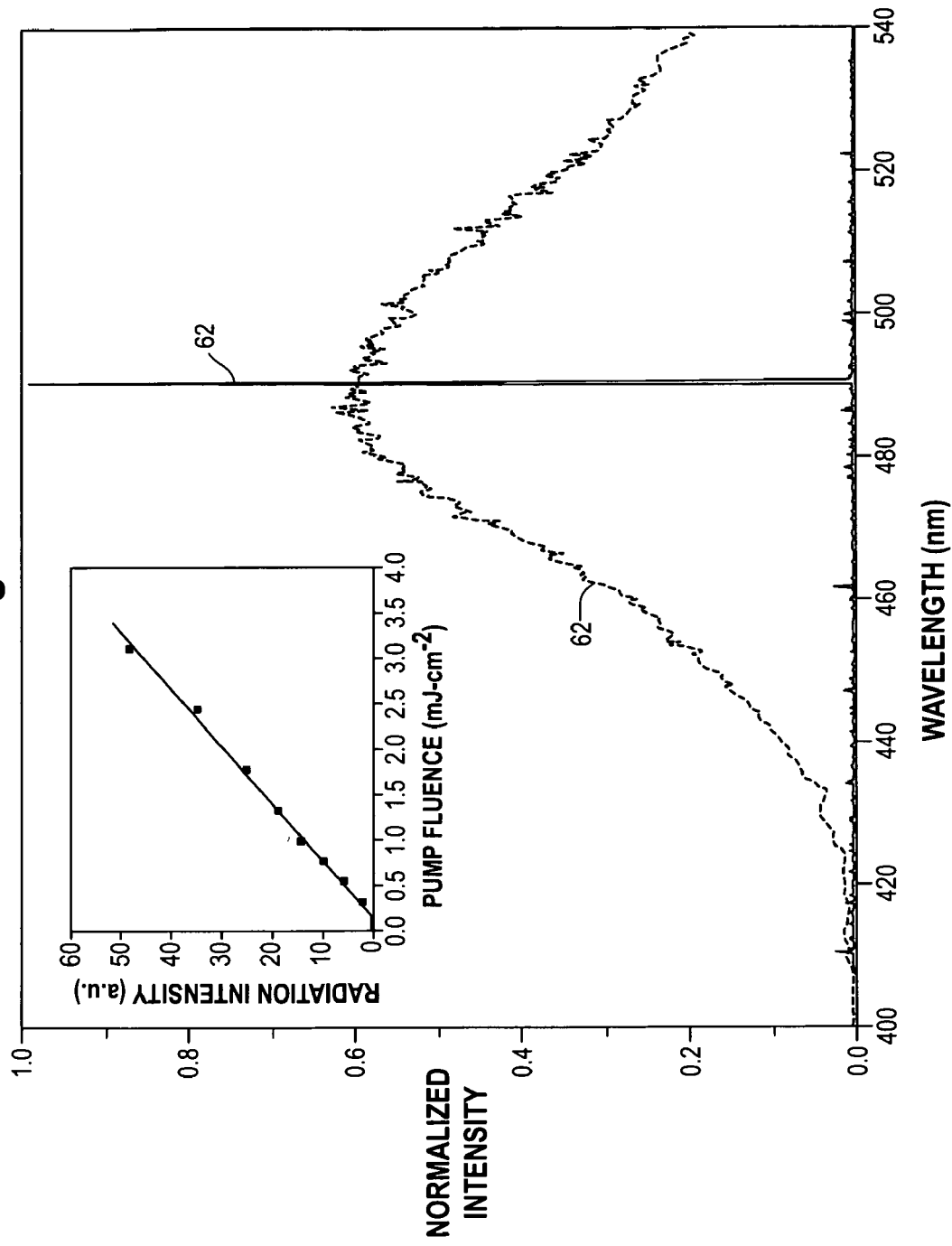

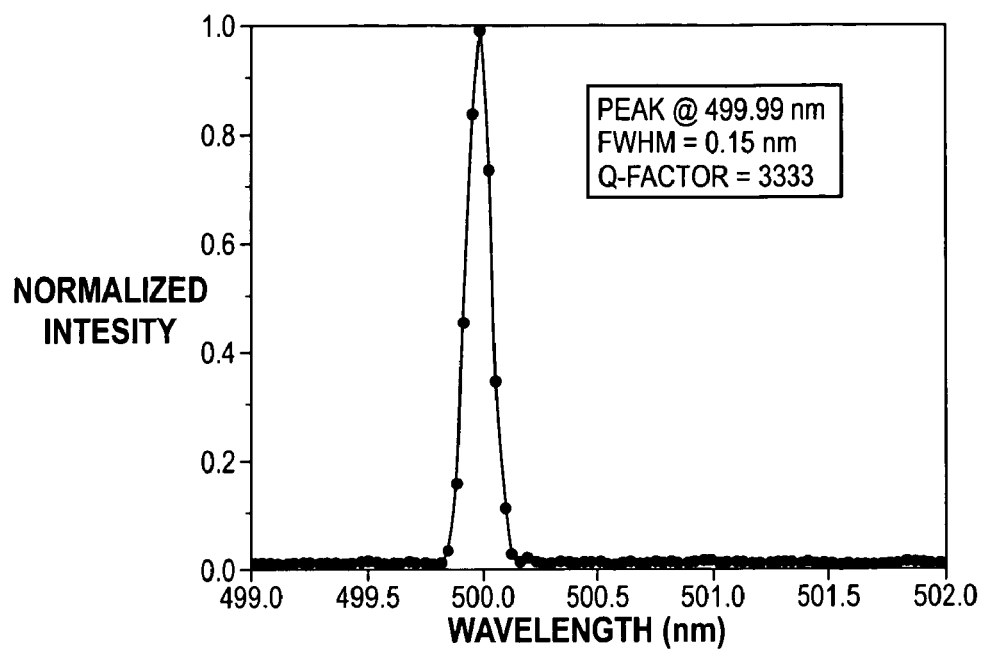
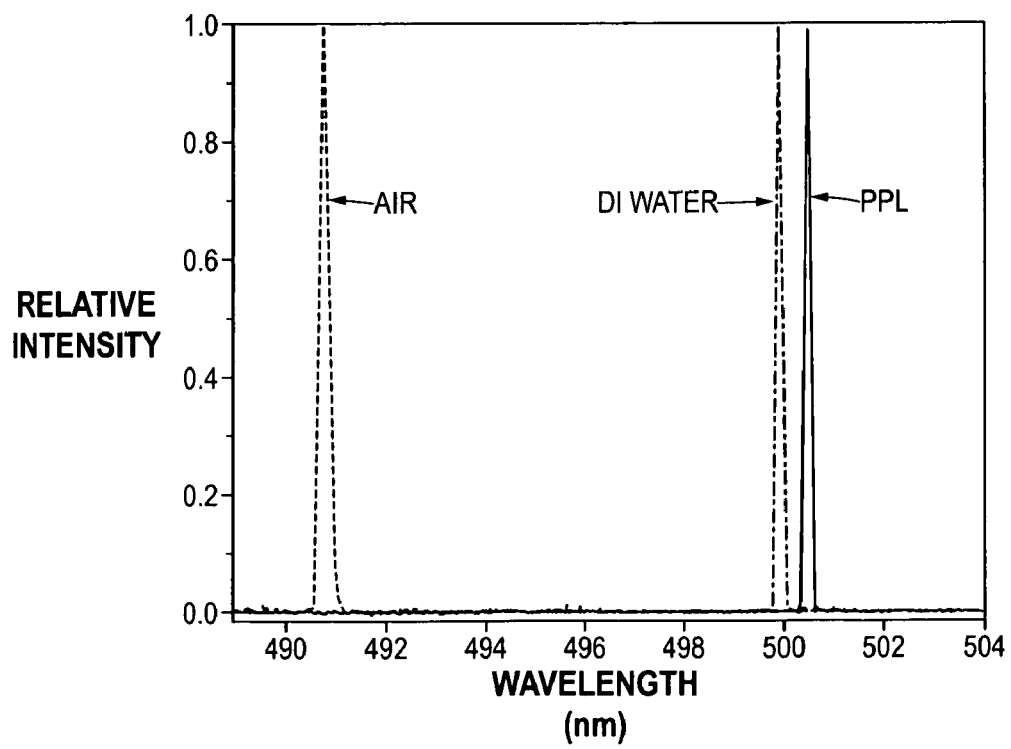

SINUSOIDAL
-NOT SHOWN OPTIONAL
HIGH INDEX LAYER

SAWTOOTH / TRIANGULAR
-NOT SHOWN OPTIONAL
HIGH INDEX LAYER

SQUARE WAVE
-NOT SHOWN OPTIONAL
HIGH INDEX LAYER

TRAPEZOIDAL
-NOT SHOWN OPTIONAL
HIGH INDEX LAYER

LABEL-FREE BIOSENSORS BASED UPON DISTRIBUTED FEEDBACK LASER

CROSS-REFERENCE TO RELATED APPLICATION

This application claims priority to U.S. Provisional Application Ser. No. 61/010,847 filed Jan. 11, 2008, the content of which is incorporated by reference herein.

BACKGROUND

Label-free biosensors based upon detecting shifts in wavelength, coupling angle, or the magnitude of optical resonances have become an effective and commercially viable means for characterizing bimolecular interactions for applications in drug discovery research, protein biomarker diagnostic testing, pharmaceutical manufacturing, and environmental monitoring.

Examples of prior art in this area include Narayanaswamy, R. & Wolfbeis, O. S. Optical sensors: industrial, environmental, and diagnostic applications. (Springer, Berlin; New York; 2004); Cunningham, B. et al. A plastic colorimetric resonant optical biosensor for multiparallel detection of label-free biochemical interactions. *Sens. Actuators, B* 85, 219-226 (2002); Homola, J., Yee, S. S. & Gauglitz, G. Surface plasmon resonance sensors: review. *Sens. Actuators, B* 54, 3-15 (1999); Armani, A. M., Kulkarni, R. P., Fraser, S. E., Flagan, R. C. & Vahala, K. J. Label-free, single-molecule detection with optical microcavities. *Science* 317, 783-787 (2007); Stewart, M. E. et al. Quantitative multispectral biosensing and 1D imaging using quasi-3D plasmonic crystals. *Proc. Natl. Acad. Sci. USA* 103, 17143-17148 (2006); Tazawa, H., Kanie, T. & Katayama, M. Fiber-optic coupler based refractive index sensor and its application to biosensing. *Appl. Phys. Lett.* 91,— (2007), and Zhang, Y., Chen, X. P., Wang, Y. X., Cooper, K. L. & Wang, A. B., Microgap multicavity Fabry-Perot biosensor. *J. Lightwave Technol.* 25, 1797-1804 (2007).

Desirable properties for such sensors include ease of fabrication over large surface areas, robust noncontact illumination/detection optics, the ability to perform many independent assays in parallel, and the ability to incorporate the sensor into common biochemical assay formats such as microplates or microfluidic channels. See Choi, C. J. & Cunningham, B. T., A 96-well microplate incorporating a replica molded microfluidic network integrated with photonic crystal biosensors for high throughput kinetic biomolecular interaction analysis, *Lab on a Chip* 7, 550-556 (2007); and Cunningham, B. T. et al. Label-free assays on the BIND system, *J. Biomol. Screen.* 9, 481-490 (2004).

Although label-free detection methods demonstrate detection resolution below 1 pg/mm$^2$, they have not replaced fluorescence and enzyme-based assays requiring the highest levels of sensitivity. The ability to resolve exceedingly small changes in the adsorbed mass density is particularly important for assays requiring the detection of samples at low concentration, or the detection of biomolecules with low molecular weight, such as drug compounds.

To address these challenges, researchers have designed label-free biosensor structures with passive optical resonators that provide a Q-factor up to $10^8$, so that smaller wavelength shifts may be resolved. See Armani, A. M. & Vahala, K. J., Biological and chemical detection using ultra-high-Q toroidal microresonators, *Biophys. J.* 29A-29A (2007); Chao, C. Y., Fung, W. & Guo, L. J., Polymer microring resonators for biochemical sensing applications, *IEEE J. Sel. Top. Quantum Electron.* 12, 134-142 (2006).

The drawbacks of extremely high Q-factor passive resonators include the requirement for precise optical alignment with the illumination source, and retaining sufficient dynamic range of wavelength shift to accommodate the detection of surface functionalization layers, immobilized ligands, and analytes.

SUMMARY

A label-free biosensor based upon a vertically emitting, distributed feedback (DFB) laser is described. In one embodiment, the DFB laser comprises a replica-molded, one dimensional dielectric grating that is coated with an active layer in the form of a laser dye-doped polymer as the gain medium. In another embodiment, the DFB laser comprises a replica-molded, one dimensional dielectric grating made from a material (e.g., polymer) that is doped with a laser dye. In this latter embodiment, the grating layer is also the active layer. Other embodiments use a thin film active layer (which may be either an organic or inorganic thin film) with a periodically varying index of refraction. The laser dye or other active material in the active layer is pumped via an external optical source, and responsively emits narrow-band, high intensity light. The sensor exhibits a high Q-factor optical resonance mode in the active layer. The stimulated emission wavelength of the laser dye is modulated, i.e., shifted, by the adsorption of biomolecules on the DFB laser biosensor's surface. In one possible example of use of the sensor, the emission spectra are monitored to quantify the kinetic adsorption of a protein polymer monolayer and sample molecule specific binding to the sensor surface.

The sensor represents a departure from conventional passive resonant optical biosensors from the standpoint that the device actively generates its own narrowband high intensity light output without stringent requirements for coupling alignment, thereby resulting in a simple, robust illumination and detection configuration. The device demonstrates high resolution for detection of small wavelength shifts, yet retains wide dynamic range.

In one embodiment, as described below in Examples 1-4, a biosensor is disclosed which, when viewed in cross-section, includes a substrate layer, a periodic surface grating layer applied to the substrate, and an active layer applied to the periodic surface grating layer. The active layer may take various forms, such as a laser dye (e.g. Coumarin, Rhodamine, DCM, and LDS), a laser dye-doped polymer (such as Polymethyl-methacrylate (PMMA), SU-8, and epoxy), a light emitting polymer (e.g. Poly-phenylene-vinylenes (PPV), Poly-phylene-ethynylenes (PPE), Polyfluorenes (PF) Ladder-type poly(p-phenylene) (LPPP), or a polymer doped with a quantum dot (e.g., ZnSe). The active layer exhibits a high Q-factor optical resonance mode when pumped with radiation above a threshold intensity level from an external source (e.g., laser pump).

In one possible embodiment, a high index of refraction material such as titanium oxide or hafnium oxide is coated onto the active layer.

The periodic surface grating may take the form of a one-dimensional periodic surface grating, or may take the form of a two-dimensional surface grating such as a two-dimensional array of posts or holes. Still other possible arrangements of the periodic surface grating are possible.

As noted above, in one configuration of the DFB laser biosensor, described below in Examples 5 and 6, the grating layer is combined with the active layer into a single layer. Thus, in this configuration, a biosensor is disclosed which includes a substrate layer, a periodic surface grating layer applied to the substrate, wherein the periodic surface grating comprises an active layer containing a substance which exhibits a high Q-factor optical resonance mode when pumped with radiation above a threshold intensity level from an external source.

In a variation of this embodiment, a high index of refraction material is coated onto the periodic surface grating.

As with Examples 1-4, the grating structure can take a variety of forms and may include one and two-dimensional gratings.

In still other embodiments described below as Examples 7 and 8, the active layer is in the form of a thin film which is deposited on a substrate and has periodically varying index of refraction in the thin film. The thin film may be made from an inorganic material, and the active substance is the active layer is a rare earth ion. In other embodiments the thin film is made from an organic material. The active layer exhibits a high Q-factor optical resonance mode when pumped with radiation above a threshold intensity level from an external source. In a variation of these embodiments, a high index of refraction material is coated onto the active layer.

In yet another aspect, methods of testing a sample are disclosed. In one form, the method includes the steps of: depositing the sample on a biosensor comprising a substrate and a periodic surface grating layer applied to the substrate, wherein the periodic surface grating comprises an active layer; pumping the active layer with an external light source at an intensity level above a threshold to produce a high Q-factor optical resonance mode in the grating layer; collecting radiation from the sensor and directing the radiation to a spectrometer; and determining a shift in the peak wavelength value of the radiation due to the presence of the sample.

In another aspect, a method of testing a sample is disclosed comprising the steps of: depositing the sample on a biosensor comprising a substrate, a periodic surface grating layer applied to the substrate, and an active layer applied to the periodic surface grating layer; pumping the active layer with an external light source at an intensity level above a threshold to produce a high Q-factor optical resonance mode in the active layer; collecting radiation from the sensor and directing the radiation to a spectrometer; and determining a shift in the peak wavelength value of the radiation due to the presence of the sample.

A system for testing a sample is also contemplated, which includes a biosensor as described herein, an optical pump (e.g. a laser or flash lamp), and a device for determining shifts in the output wavelength from the biosensor. The device for determining shifts in the output wavelength from the biosensor can take various forms, including for example various types of spectrometers, and ultrahigh resolution spectrographic devices, such as for example described in U.S. Pat. No. 7,310,153.

BRIEF DESCRIPTION OF THE DRAWINGS

FIG. 1 is a schematic diagram of the sensor structure in accordance with an illustrated embodiment and the associated pumping and detection system. The grating structure has a periodicity $\Lambda=360$ nm, depth d=40 nm, and RI of 1.17. The dye-doped polymer layer and high refractive index (RI) dielectric coating have a thickness of $t_g$ and $t_c$, respectively. The sensor chip is optically pumped with Nd:YAG laser ($\lambda=355$ nm) and the emission from the active layer is coupled to a spectrometer through an optical fiber.

FIGS. 2A-2D are illustrations of the simulated electric field intensity distributions that are associated with a resonant mode within a single period of a grating structure of the design of FIG. 1. A cross-section of the sensor is shown above each of the simulated electric field distributions of FIGS. 2A-2D for reference. The sensor surfaces are aligned at y=0 for all plots. In FIG. 2A, the substrate grating layer is formed within an epoxy material. In FIG. 2B, the epoxy material used in FIG. 2A is replaced with low RI nano-porous glass. The resonant mode moves closer to the sensor surface. In FIG. 2C, the thickness of the glass layer ($t_g$) is reduced from 500 nm to 350 nm. In FIG. 2D, a 40 nm high RI dielectric coating comprising a $HFO_2$ film is coated on top of the active layer.

In FIG. 3A, spontaneous emission (dashed line) and laser spectrum (solid line) for the DFB laser were recorded for pump energies below and above a threshold, respectively.

FIG. 4A shows the normalized laser emission spectra as the sensor surface is in an Air environment, DI water environment, and PPL solution environment, respectively. FIG. 4B shows the time-dependent PWV values for a PPL monolayer deposited onto the DFB laser sensor surface. The stabilized surface shift for DFB laser based biosensor is 0.53 nm.

FIG. 5A shows the kinetic PWV plot of the streptavidin immobilization process onto the sensor surface that was pre-treated with a specific surface chemistry protocol.

FIG. 5B shows the detection of biotin binding with the immobilized SA. The stabilized PWV shift is around 54 picometers (pm).

FIG. 7A is a plot of the spontaneous emission (dashed line) and laser spectra (solid line) for the DFB laser of FIG. 6, recorded for pump fluences below and above a threshold, respectively. The inset plot shows the dependence of the relative laser output power on the pump fluence. Using least-squares fit to the experimental data, the threshold fluence for the resonance mode lies at 1.8 $\mu J$-$mm^{-2}$.

FIG. 7(b) is plot of the experimentally measured radiation spectrum of the sensor of FIG. 6, with the sensor surface immersed in DI water.

FIG. 8 is a plot of the normalized laser emission spectra as sensor surface soaked in Air, DI water, and PPL solution, respectively for the sensor of FIG. 6. The sensor was pumped at a fluence of 10.2 $\mu J$-$mm^{-2}$ for all three measurements.

DETAILED DESCRIPTION

Figure 2E:
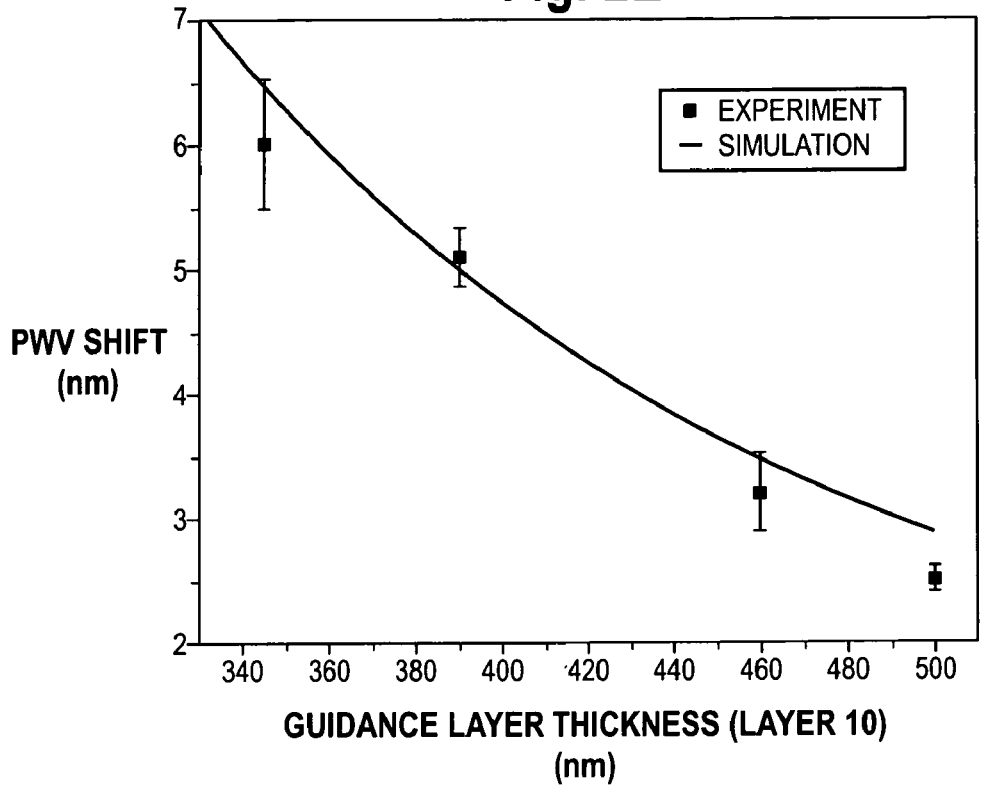
FIG. 2E is a plot of the shift in peak wavelength value (PWV) as a function of gain layer thickness in nanometers, for both a simulation of the sensor and an experiment. In the experiment, the sensor surface was exposed to air and subsequently to deionized (DI) water. The plot shows the PWV shifts in terms of $t_g$ changes from 340 nm to 500 nm.

This invention is directed to a distributed feedback (DFB) laser that is designed to function as a label-free optical biosensor. The biosensor includes a periodic surface grating structure which includes an active layer containing a dye material which lases (emits high intensity narrow band light) upon optical excitation (pumping) from an external light source, e.g., a laser, or flash lamp. The active layer can be considered a DFB laser cavity in the form of a corrugated waveguide containing an active gain medium. The geometry and refractive index (RI) of the DFB cavity determines the resonant wavelength. The emission wavelength satisfies the Bragg condition, $\lambda_m = 2\Lambda n_{eff}/m$ where m is the diffraction order, $\Lambda$ denotes the grating period, and $n_{eff}$ represents the effective RI that is modulated by biomolecular adsorption on the sensor surface.

A label-free sample, e.g., biomolecular material or drug, is bound to the upper surface of the sensor. Lasing is obtained by optical excitation ("pumping") of the dye material that is incorporated within the active layer of the DFB sensor. The output laser light is collected by a wavelength-detection instrument such as a spectrometer. The laser output wavelength is tuned, i.e., shifted, by the adsorption of biomolecular material on the surface of the sensor structure, where the change in wavelength is proportional to the mass density of deposited material. The DFB laser structure may be fabricated over large surface areas using a replica molding process, and incorporated into any liquid handling device used for biological experiments, including microtiter plates and microfluidic channels.

A primary application of the disclosed device is detection of adsorbed biomaterial on the surface of the transducer, without requiring the use of stains, dyes, or other label. Detected biomaterial can include proteins, small molecules, single strand DNA, double-strand DNA, antibodies, antibody fragments, virus particles, spores, bacteria, and cells.

In a typical embodiment, a chemoselective substance (molecule) is attached to the sensor surface which has the ability to selectively bind with a second molecule in a test sample. In this fashion, the sensor may be used to selectively detect and/or identify a wide variety of biological analytes. The sensor surface may be populated with an array of immobilized molecules, and different locations of the array may be measured separately so that many binding events can be measured in parallel.

Applications include assays used in pharmaceutical research, detection of specific DNA sequences or proteins in a test sample from a human, animal or plant subject for purposes of diagnostic tests. Additional applications include detection of pathogens in the environment.

DFB laser biosensors described in this disclosure have the several features:

(1) Unlike "passive" optical biosensors that simply reflect or transmit light that is incident upon them, the DFB laser biosensor actively generates its light output by stimulated emission.

(2) The light emitted by the DFB laser biosensor is contained within an extremely narrow band of wavelengths, leading to the ability to resolve very small changes in the emitted wavelength. The biosensor resonance can be considered to have a high "Quality Factor" or "Q Factor" (or just "Q") compared to other optical biosensors.

(3) The high Q of the biosensor leads to the ability to resolve extremely small changes in the mass density of biomolecules adsorbed on the surface.

(4) Although the device has a very high Q factor for high resolution, it simultaneously provides high sensitivity and a high dynamic range. Sensitivity is defined as the amount of laser wavelength shift resulting from a fixed change in adsorbed mass density. High sensitivity combined with the ability to resolve small changes in mass density results in a favorable "Figure of Merit" as defined by the ratio of sensitivity to the resolution. High dynamic range is required for practical use as a biosensor, as the sensor must provide wavelength shift response not only to the detected biomolecule, but also to the immobilized molecule and any surface chemistry films that are used to covalently attach the immobilized molecule to the surface and to block the non-specific adsorption of unwanted molecules.

(5) The laser output occurs in a direction normal to the transducer surface, so the light may be easily gathered with fiber optic probes and analyzed from many separate locations on the surface.

(6) The device may be fabricated using either glass or plastic-based materials and processes using a replica molding fabrication approach that can be performed accurately over large surface areas. Plastic-based processes may be adapted to be performed on continuous rolls of flexible plastic film. Several fabrication methods are described that result in an inexpensive manufacturing process.

(7) The device may be easily integrated with standard format microplates, glass microscope slides, or networks of microfluidic channels.

Example 1

FIGS. 1-5B

A cross-sectional diagram (not to scale) of the DFB laser sensor 1 in a first example is shown in FIG. 1. A low index of refraction dielectric material 8 is formed as a periodic one or two dimensional grating on the surface of a dielectric substrate 16 by replica molding, in a manner known in the art and described in the patent literature. See, for example, Schulz et al., U.S. Pat. No. 7,162,125; Cunningham et al., U.S. patent application publication 2003/0027327, the contents of both of which are incorporated by reference herein. A dye-doped polymer active layer 10 (also referred to herein as a "guidance layer" or "gain layer") is then spin-cast coated onto the upper surface of the grating layer dielectric material 8. The dye-doped polymer active layer 10 serves as the waveguide layer, in that resonance modes produced in the sensor are confined within the active layer 10. Finally, a high RI thin film 12 is deposited on the top surface. A sample 14 (e.g., protein, biomolecule, drug, water sample, PPL, streptavidin, etc.) is deposited on the top surface of the structure of FIG. 1.

The DFB laser biosensor 1 may be optically pumped from above or below at any incident angle by a laser 20. The resulting stimulated emission 22 is captured at normal or near-normal incidence by an optical fiber 24 which is coupled to a spectrometer. The optical pump may also take the form of a flash lamp, a pulsed laser and a continuous wave (CW) diode laser. The selection of the type of optical pump will depend on such factors as the active substance in the active layer, and the photon lifetime in the active layer (i.e., how rapidly the resonance mode decays).

The pumping of the dye-doped polymer layer 10 produces lasing in the sensor 1 and in particular a resonant mode in the layer 10, characterized by spatially localized regions of high electric field intensity. The resonance mode features a narrow wavelength band and high Q factor. By manipulating the spatial distribution of the resonance mode, it is possible to optimize the sensor sensitivity. The goal is to increase the overlap between the resonance mode and the biomolecular material 14 adsorbed to the upper surface of the sensor 1, while maintaining a substantial part of the mode within the gain layer 10 to facilitate lasing. Rigorous Coupled Wave Analysis (RSoft) was used to numerically predict the resonant wavelength and the associated mode pattern of the device of Example 1. The calculated electric field intensity distributions, (i.e. resonant mode pattern) within one period of the grating are compared in FIG. 2a-d for four exemplary sensor designs, some of which are variations from the structure of FIG. 1 as will be explained below.

FIG. 2A shows the mode distribution for a sensor design in which the grating is replicated with epoxy (layer 8) of RI=1.47. The dye-doped polymer layer 10 has a RI=1.51 and a thickness of 500 nm. As the first modification, the epoxy layer 8 is replaced by a lower RI (RI~1.17), nanoporous glass layer 8 (see FIG. 2b). Compared to the mode shape given in FIG. 2A, the resonant mode shown in FIG. 2B is closer to the sensor surface. In the embodiment of FIG. 2C, the dye-doped polymer layer 10 thickness is reduced from 500 nm to 350 nm. FIG. 2C shows an extension of the resonant mode above the sensor surface when this modification to the cavity is implemented. In FIG. 2D, an additional optimization is achieved by adding a high RI thin film coating 12, such as hafnium dioxide ($HfO_2$; RI~2.0 at $\lambda$=500 nm). Coating the sensor surface with a 40 nm thick $HfO_2$ film draws the resonance mode closer to the sensor surface and improves the mode's spatial overlap with the biomolecule adsorption region.

Figure 2F:
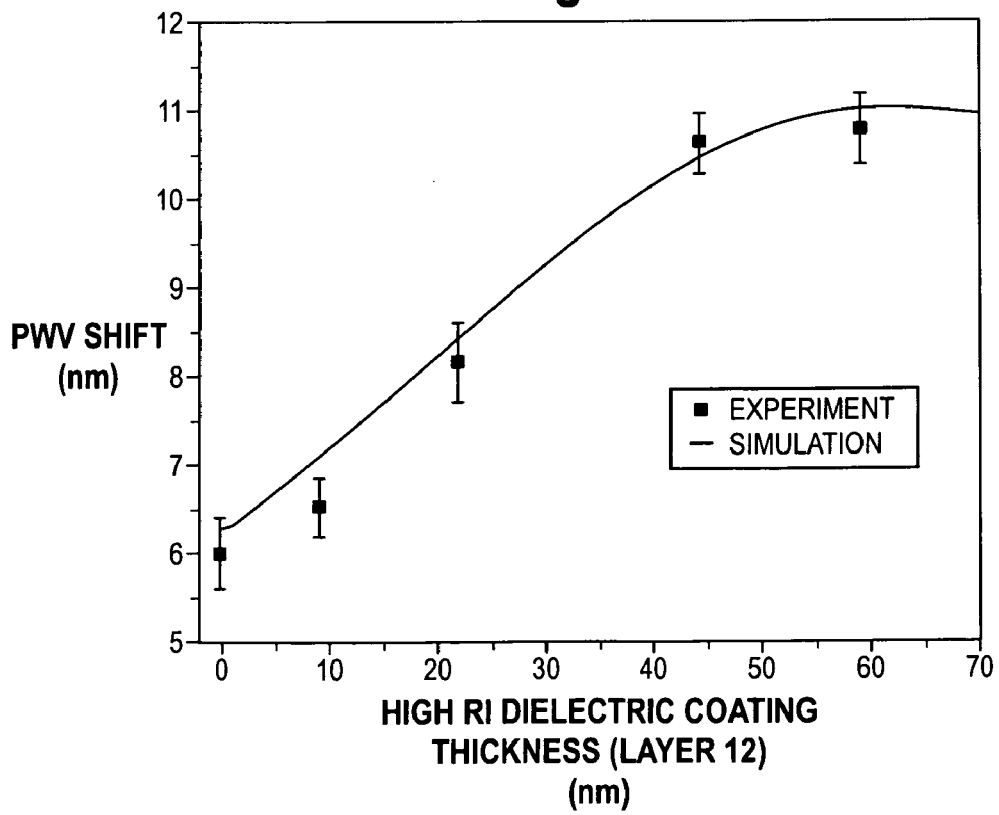
FIG. 2F is a plot of the shift in peak wavelength value (PWV) as a function of the dielectric layer thickness (in nanometers). The same PWV shifts were investigated with $t_c$ varies from 0 to 70 nm.

To verify the modal analysis, the emission wavelength shift caused by the changes in the RI of the bulk material exposed to the sensor surface was numerically and experimentally studied. The sensor surface was first exposed to air (RI~1.0), and subsequently to water (RI~1.33). FIGS. 2E and 2F illustrate the shift of the DFB laser peak wavelength (PWV) (DFB laser emission 22 in FIG. 1) wavelength corresponding to several values of the guidance layer 10 (FIG. 2E) or $HfO_2$ layer 12 thicknesses (FIG. 2F) ($t_g$ and $t_c$, respectively). By reducing $t_g$ and increasing $t_c$ values, the sensor sensitivity was enhanced by a factor of 4.5. On the other hand, excessive reduction of the guidance layer 10 thickness, or an excessively thick $HfO_2$ coating layer 12 will result in a high lasing threshold, because the DFB laser also requires overlap of the cavity mode with the gain medium.

Figure 3A:
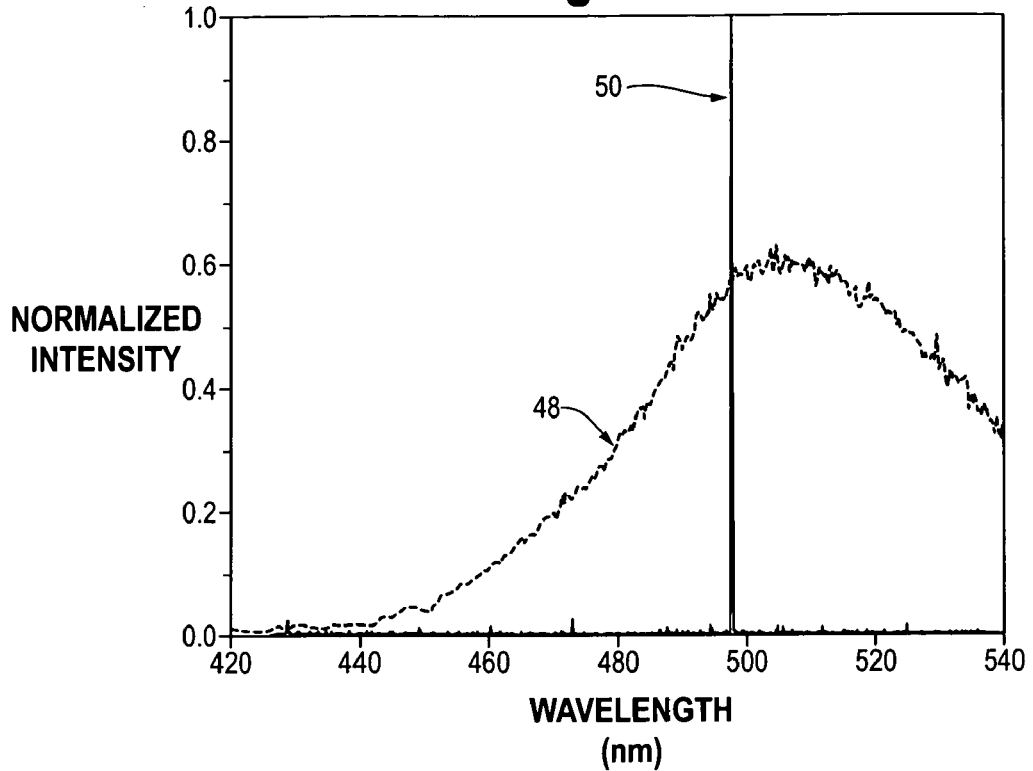
FIG. 3A is a plot of the DFB laser emission spectra for the sensor of FIG. 1.
Figure 3B:
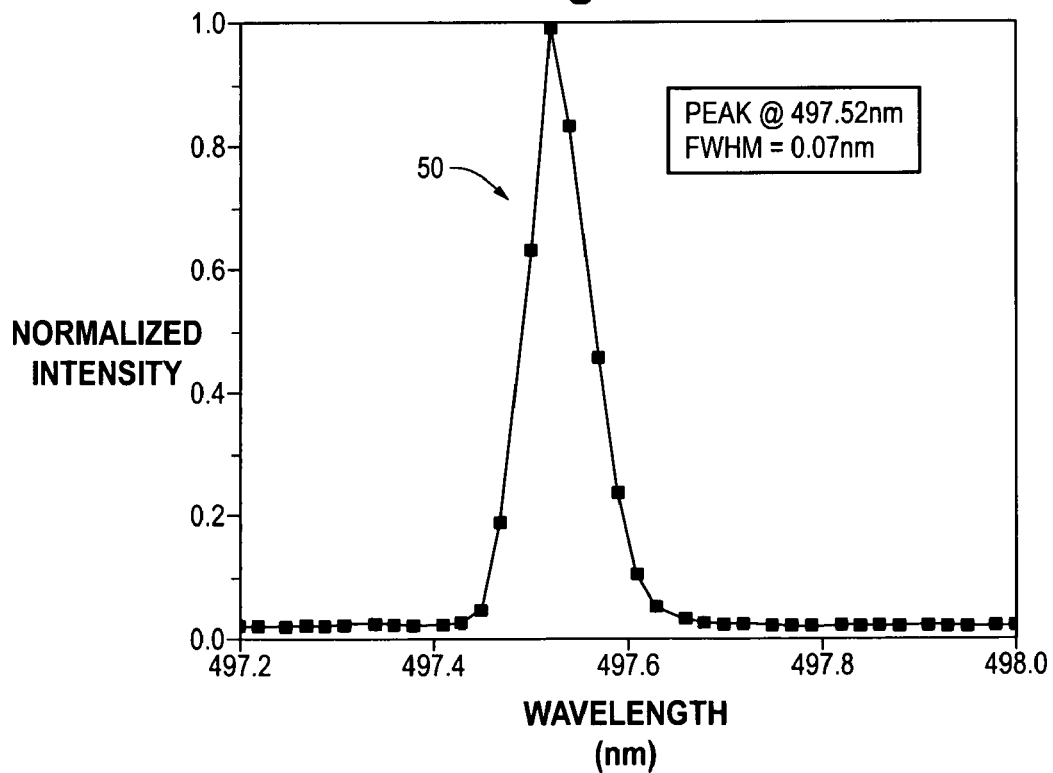
FIG. 3B is an inset figure for FIG. 3A showing in greater detail the spectrum in the region between 497 and 498 nm (i.e., the sharp peak in FIG. 3A), when the device was excited at 5.5 $\mu J$-$mm^{-2}$.

An example of a preferred embodiment in Example 1 consists of the nanoporous glass grating layer 8 applied to a substrate, with the grating periodicity $\Lambda$=360 nm and grating depth d=40 nm), the laser dye (Coumarin 503) doped organic gain layer 10 ($t_g$=350 nm, RI=1.51), and the $HfO_2$ coating layer 12 ($t_c$=40 nm). The sensor is excited by a frequency-tripled Nd:YAG laser ($\lambda$=355 nm) producing pulses in the fundamental transverse mode with durations of ~8 ns FWHM (full wave half maximum). With the DFB laser surface exposed to air, spectra representative of those recorded for pump fluences of 0.8 $\mu$J-mm$^{-2}$ and 5.5 $\mu$J-mm$^{-2}$ are presented in FIG. 3. The curve for the pump fluence of 0.8 $\mu$J-mm$^{-2}$ is shown by the curve 48, which is below the lasing threshold. At higher intensities, laser oscillation occurs at $\lambda$=497.53 nm (indicated by the peak 50) with FWHM~0.07 nm. The laser threshold fluence is ~1.8 $\mu$J-mm$^2$. Note the extreme sharpness of the peak 50, indicating the high Q factor of the resonance mode. FIG. 3B shows the peak 50 in greater detail.

Figure 4A:
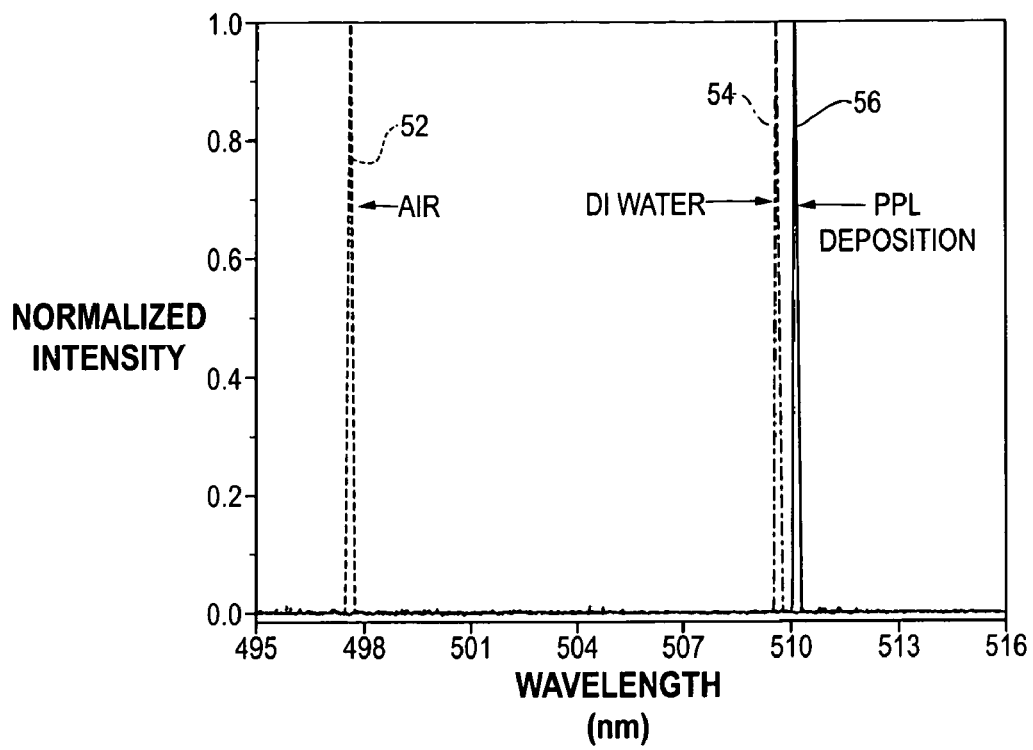
FIGS. 4A and 4B are plots of the spectral signature and kinetic PWV shift for the sensor of FIG. 1.

FIG. 4A illustrates measurements of radiation spectra when the device surface of Example 1 was exposed to air (peak 52), submerged in deionized (DI) water (peak 54), and coated with a monolayer of protein polymer Poly(Lys, Phe) (PPL; 0.5 mg/mL; Sigma-Aldrich) solution (peak 56). The peak wavelengths were measured as 497.52 nm, 509.64 nm, and 510.18 nm, respectively. The spectral width of the laser remains narrow $\Delta\lambda$<0.1 nm) throughout the experiments. Sensitivity to surface mass adsorption was characterized by adding the PPL solution, which has been shown to deposit a self-limited, single ~15 nm thick monolayer with a RI of 1.45 and a mass density of ~2.5 ng/mm$^2$ The sensor exhibited a wavelength shift of 0.53 nm for the adsorption of the PPL.

Figure 4B:
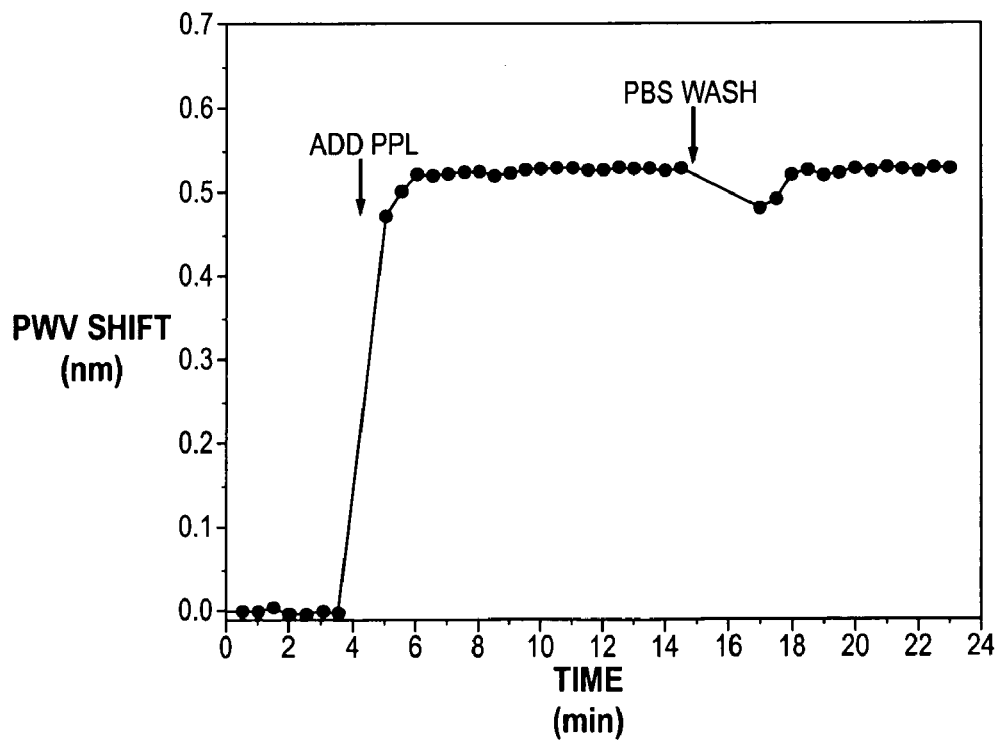

By taking several measurements with the same sensor as a function of time, the kinetic characteristics of mass adsorption can be determined, as shown in FIG. 4B for the dynamic detection of the growth of a single PPL layer. Initially, a baseline value for the laser wavelength was established with the sensor surface soaked in phosphate buffered saline (PBS) solution. After 4 minutes, the PBS solution was replaced with a PPL solution and stabilized for 10 min. Then the sensor surface was rinsed with PBS solution to remove any PPL that is not firmly attached to the sensor. The sensor produced a wavelength shift of 0.53 nm for PPL monolayer adsorption, and exhibited no detectable drift over time periods up to one hour.

Figure 5A:
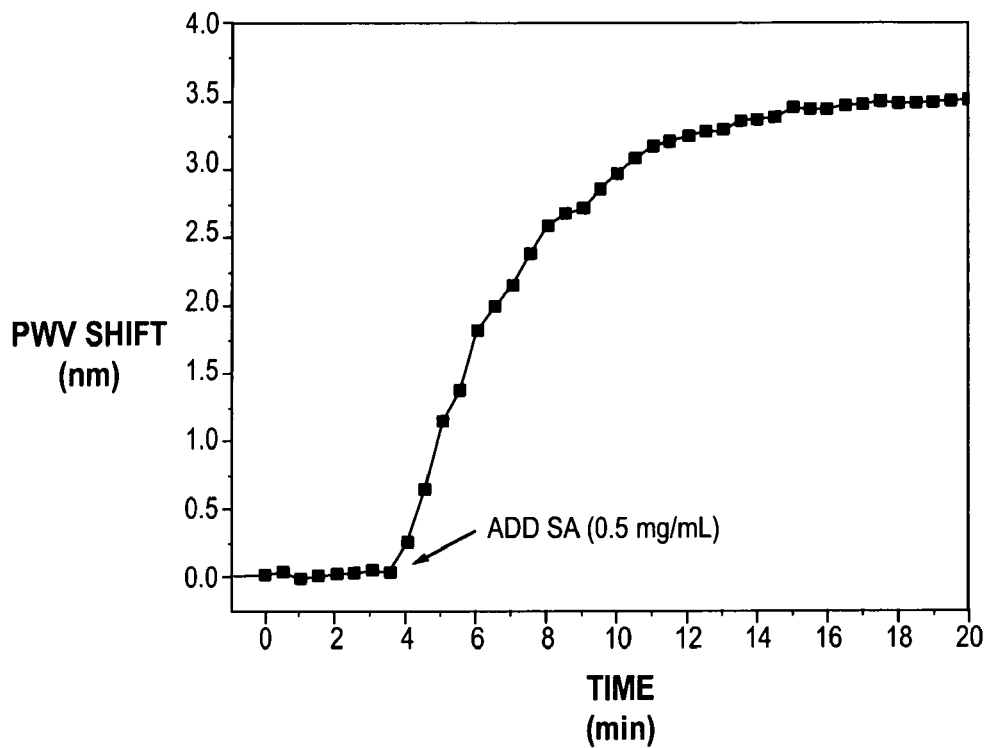
FIG. 5A is a plot showing the shift in PWV as a function of time for the sensor of FIG. 1, with streptavidin (SA) added to the sensor at four minutes.
Figure 5B:
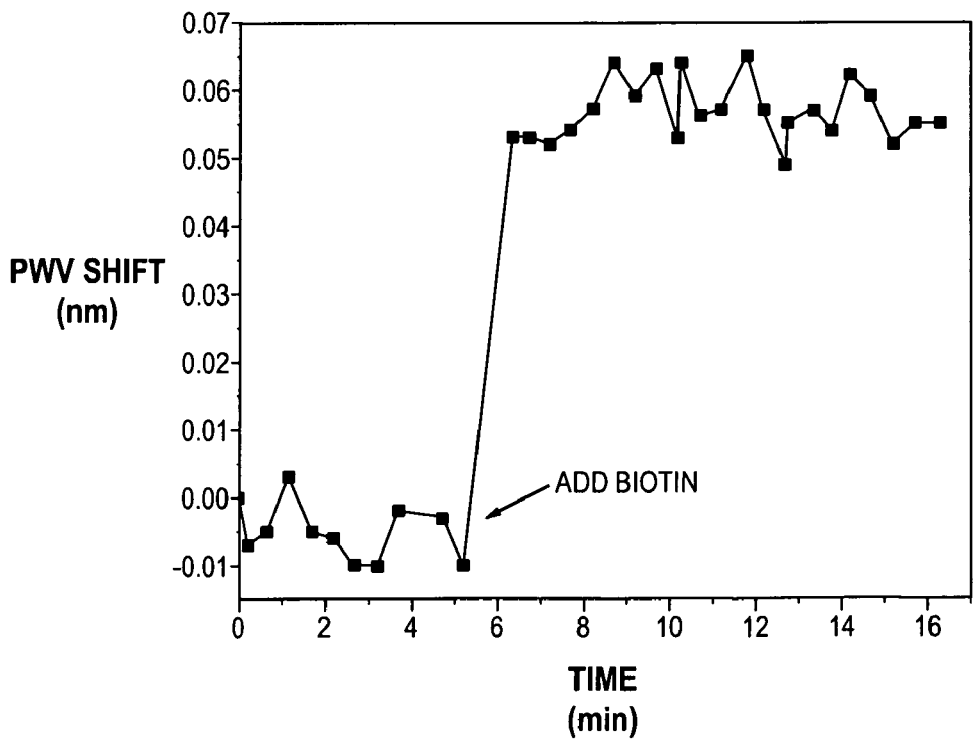
FIG. 5B is a plot showing the shift in PWV as a function of time for the sensor of FIG. 1, with biotin added to a sensor in which streptavidin was previously applied to the sensor and bound to the surface. The biotin was added at approximately five minutes.

A common test for characterizing biosensor performance is to immobilize a large molecule ("chemoselective layer") that is subsequently the vehicle for capturing a much smaller molecule. As a simple demonstration of this concept, we immobilized streptavidin (SA) (MW=60,000 Da) on the sensor, pre-treated by covalent surface chemistry (see Methods, below), as a precursor to the detection of biotin (MW=244 Da). The DFB laser wavelength was monitored during the first 16 minutes of the SA (0.5 mg/mL; in DI water) immobilization process and the results are shown in FIG. 5A. After 30 hours SA incubation, the sensor chip was rinsed with DI water. While immersing in 100 µL DI, the sensor chip was stabilized for 5 minutes. Upon adding 5 µL biotin (0.25 mg/mL; in DI water), the kinetic binding process shown in FIG. 5B was observed. The binding of biotin to SA produced a laser wavelength shift of $\Delta\lambda=54$ picometers (pm).

The minimum detectable laser wavelength shift was determined by exposing the sensor to DI water and measuring the wavelength every 100 ms for a total period of 10 seconds. Since the wavelengths were found to vary from 508.158 nm to 508.168 nm with a standard deviation ($\sigma$) of 2.2 pm, the system resolution was found to be $\Delta\lambda=3\sigma=6.6$ pm. For these measurements, the minimum detectable wavelength shift is limited by the wavelength resolution of the spectrometer, as the narrow laser emission peak is detected by only 2-3 pixels. The high intensity, narrow linewidth output of the DFB laser sensor will afford the capability for resolving even smaller wavelength shifts using alternate wavelength measurement methods (such as a higher resolution conventional spectrometer, or graded-wavelength filter spectrometers). See Ganesh, N., Xiang, A., Beltran, N. B., Dobbs, D. W. & Cunningham, B. T., Compact wavelength detection-system incorporating a guided-mode resonance filter. *Appl. Phys. Lett.* 90,—(2007); Kiesel, P., Schmidt, O., Mohta, S., Johnson, N. & Malzer, S. Compact, low-cost, and high-resolution interrogation unit for optical sensors. *Appl. Phys. Lett.* 89, (2006).

In summary, this application describes the first reported use of a DFB laser biosensor for label-free optical bioassay detection. The demonstrated DFB laser biosensor exhibits single mode operation and a spectral linewidth of 0.07 nm. The biosensor has a surface sensitivity that results in a laser wavelength shift of 0.53 nm in response to the adsorption of a monolayer of PPL. The DFB laser sensor kinetically detects a shift of ~0.06 nm as a result of biotin binding on the SA immobilized sensor surface. The sensor system is capable of resolving wavelength shifts as small as 6.6 pm with accuracy over 99%. Because the replica molding process is inexpensive and scalable to large areas, and the DFB grating structure is amenable to simple yet robust excitation and output detection methods, this type of sensor is expected to become practical for applications demanding high sensitivity in life science research, diagnostic testing, and environmental detection.

Methods

Fabrication

A flexible PDMS mold was used for imprinting the device grating pattern in nanoporous glass which was itself defined from a silicon "master" mold. The master mold was produced on a 4-inch diameter silicon wafer by deep UV-lithographic and dry etching processes. As verified by atomic force microscopy, the replicated gratings (layer 8) on the finished device have a periodicity and depth of 360 nm and 40 nm, respectively. The dye-doped polymer layer 10 was fabricated by preparing a 15 mg/mL solution of Coumarin 503 dye (Exciton) and methyl chloride mixed in solution with Poly (methyl methacrylate) (PMMA) solution (4% PMMA solid dissolved in chlorobenze) to a volume percentage of 30%. This material was sonicated for improved homogenization and subsequently spin-coated onto the dielectric grating/substrate assembly (8/16) at 4000 rpm for 30 seconds. The device was baked on a 110° C. hotplate for 1.5 min to vaporize the solvent and densify the film. The sensor was finally coated with an ~40 nm thick $HfO_2$ film (layer 12) using an electron beam evaporator (Denton Vacuum). The film thickness and RI were measured by ellipsometry (VASE, J. A. Woollam). The sensor was attached to a conventional bottomless 96-well microplate with adhesive, allowing individual wells to be filled with liquid.

Sensor Measurement

The biosensor 1 is excited by ~8 ns pulses from a frequency-tripled, Q-switched Nd:YAG laser ($\lambda=355$ nm) in the single pulse mode. Each output pulse from the DFB laser is coupled to a spectrometer (HR4000, Ocean Optics; FWHM resolution $\Delta\lambda=0.05$ nm) through an optical fiber. The Nd:YAG laser and spectrometer are simultaneously triggered by software control. To determine the peak wavelength of the laser spectrum with maximum resolution, the captured laser spectra were fitted to a standard Lorentzian distribution function and the peak value was determined from the fitted parameters.

Surface Chemistry Protocol

The $HfO_2$-coated sensor 1 was first immersed in a proprietary amine polymer solution for 24 hours followed by DI water washing. The second step involves exposing the surface to glutaraldehyde (GA; $C_5H_8O_2$; 25% in DI water) for 3.5 hours. The GA functionalizes the amine groups in the amine polymer film and enables subsequent attachment of streptavidin (the chemoselective layer). The streptavidin solution (0.5 mg/mL in DI water) was added to the sensor-surface and allowed to incubate for 30 hours at 4° C.

Example 2

Figure 6:
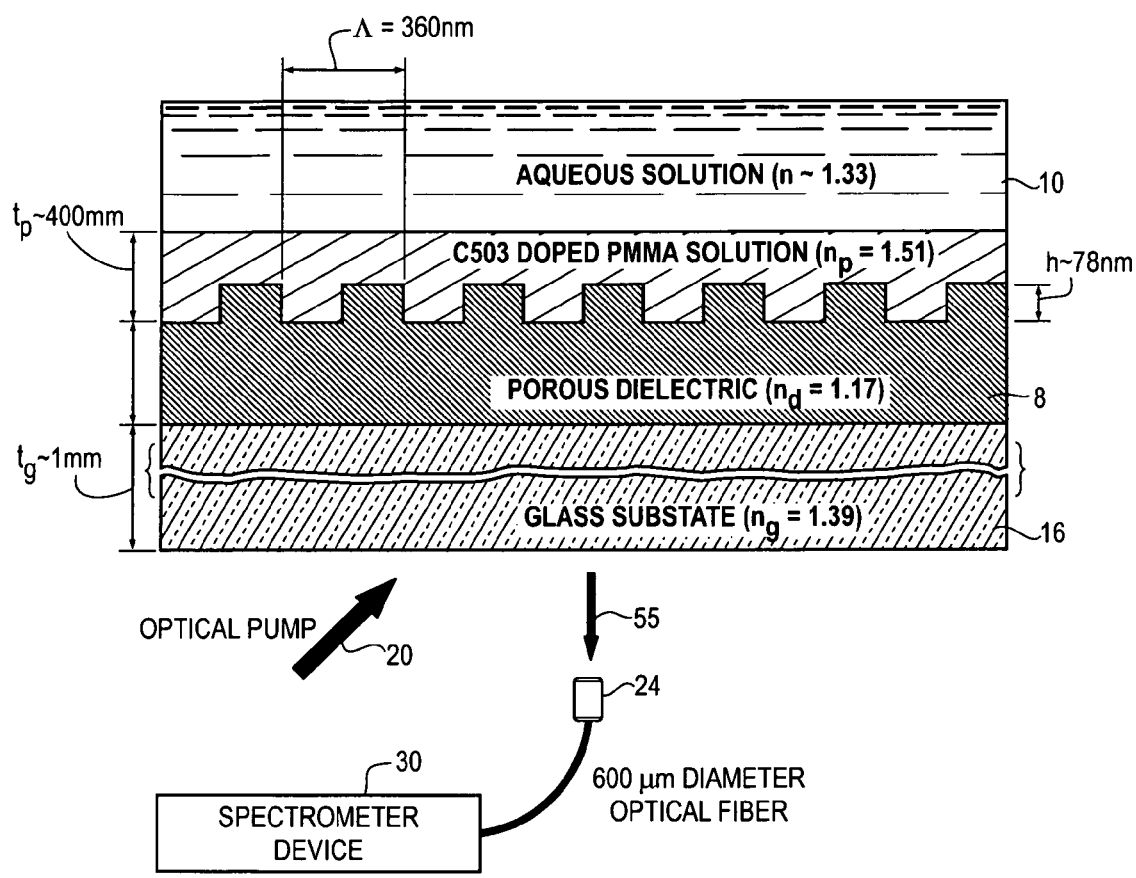
FIG. 6 is a cross-sectional illustration of a second embodiment of a DFB sensor.

A cross-sectional diagram (not to scale) of a second example of a DFB laser sensor is shown in FIG. 6. The structure includes a glass substrate layer 16 (approximately 1 mm in thickness), a grating layer 8 formed on the surface of the substrate 16, and a C503 dye-doped active layer 10 deposited on the grating layer 8. The grating layer is a nanoporous spin-on glass (with index of refraction n=1.17) which is formed on the substrate 16 using a polydimethylsiloxane (PDMS) mold bearing a negative volume image of the desired grating pattern upon a 2×3-inch glass substrate 16. The flexible PDMS mold used for imprinting the device grating pattern was itself molded from a silicon "master" mold. The master mold was produced on a 4-inch diameter silicon wafer by conventional photolithographic and dry etching processes. Verified by atomic force microscope, the replicated gratings on the finished device have periodicity and depth of 360 nm and 78 nm, respectively. The waveguide layer 10, i.e. gain medium, was fabricated by preparing a 20 mg/mL solution of Coumarin 503 dye (Exciton) and $CH_2Cl_2$ mixed in solution with PMMA (950 PMMA C resist, Microchem) to a volume percentage of 30%. This material was sonicated for improved homogenization and subsequently spin-coated onto the dielectric grating/substrate assembly at 4000 rpm for 30 seconds. The device was baked on a 110° C. hotplate for 2 min to remove the solvent from dye doped PMMA layer and harden the film. Finally, the PMMA surface was exposed to $O_2$ plasma for 30 sec for final surface cleaning, leaving the surface in a hydrophilic state. The completed DFB active layer 10 has an overall thickness of ~400 nm and refractive index of n=1.51 as measured by ellipsometer (VASE, J. A. Woollam).

Device characterization was conducted by exciting the Coumarin 503 with 10 ns pulses from a frequency-tripled, Q-switched Nd:YAG laser (20) (λ=355 nm) at a repetition rate of 10 Hz. The laser emission 22 emanating from the DFB grating was coupled to a spectrometer 30 (HR4000, Ocean Optics) through an optical fiber 24. The spectrometer has a spectral resolution of DI=0.09 nm full wave half maximum (FWHM). With the DFB laser surface exposed to air ($n_a$=1.0), spectra representative of those recorded for pump fluences of 0.8 μJ-mm$^{-2}$ and 8.5 μJ-mm$^{-2}$ are presented in FIG. 7(a). For a fluence below threshold (0.8 μJ-mm$^{-2}$), the fluorescence from the dye/polymer matrix is broad (DI ~70 nm FWHM), indicated by the curve 60. At higher fluescence intensities, laser oscillation occurs at λ=490.77 nm, indicated by the sharp peak 62. Using a pyroelectric detector, the dependence of the relative DFB laser pulse energy on the pump fluence was recorded and plotted in the inset of FIG. 7(a). A clear threshold fluence of ~1.8 μJ-mm$^{-2}$ is observed and, above threshold, the output rises linearly with pump power as exhibited by the linear least-squares fit to the pump fluence F≧1.8 μJ-mm$^{-2}$ data. FIG. 7(b) illustrates the spectra of the laser emission when the sensor surface was immersed in DI water ($n_{DI}$=1.33) with pump fluence of 10.2 μJ-mm$^{-2}$. The laser emission wavelength shifts to l=499.99 nm and exhibits a linewidth of DI=0.15 nm, resulting in a Q-factor of 3333.

In order to measure the sensitivity of the laser wavelength to changes in the refractive index of the "bulk" material exposed to the upper surface, the emission spectra was first obtained with the surface exposed to air, and subsequently to water. Sensitivity to surface mass adsorption was characterized by adding a solution of the protein polymer Poly(Lys, Phe) (PPL; Sigma-Aldrich), which has been shown to deposit a self-limited single ~15 nm thick monolayer with a refractive index of n~1.45 and a mass density of ~2.5 ng/mm$^2$. FIG. 8 illustrates measurements of radiation spectra when the device surface of Example 2 was exposed to air, submerged in DI water, and exposed to PPL solution, respectively. The peak wavelength values (PWV) were measured as 490.77 nm, 499.99 nm, and 500.52 nm, respectively. The FWHM values of peak profile remains narrow (DI<0.18 nm) throughout the experiment, indicates that FWHM is insensitive to the surface refractive index changes. The bulk refractive index sensitivity was determined by measuring $S_b$=ΔPWV/Δn. Based on the air/water transition, the DFB laser sensor has $S_b$=27.9 nm per refractive index unit (RIU).

Figure 9:
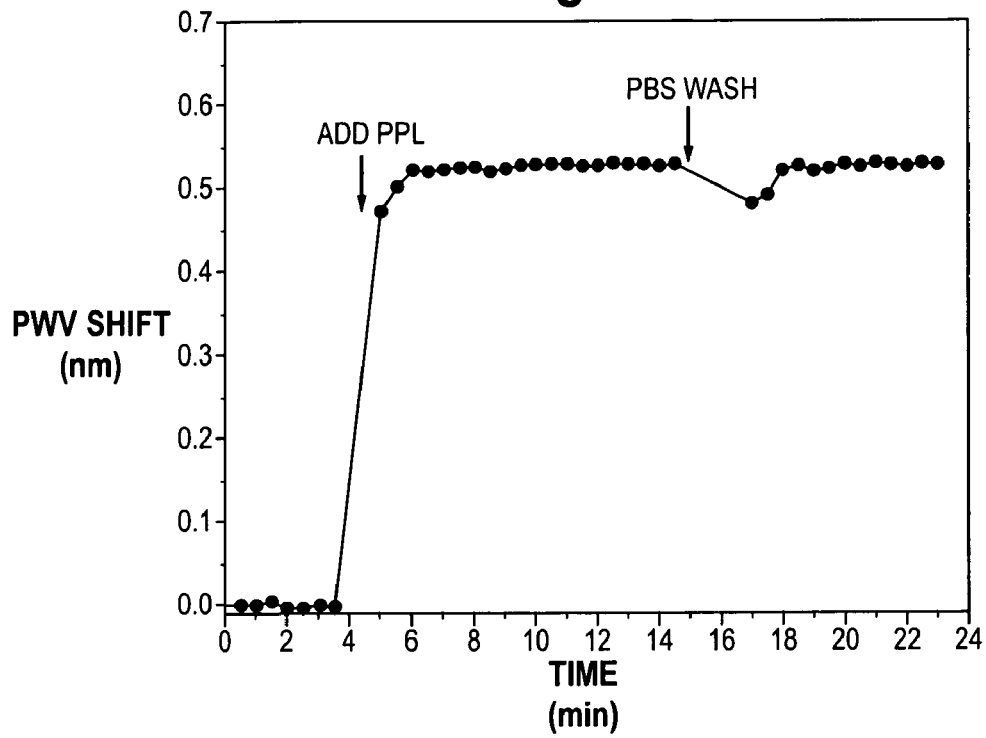
FIG. 9 is a kinetic plot of PWV shift for PPL monolayer deposited onto the DFB laser sensor surface of FIG. 6. During the experiments, the pump fluence was kept constant at 12.5 µJ-mm$^{-2}$. The stabilized surface shift for DFB laser based biosensor is 0.53 nm.

By taking several measurements of the same sensor as a function of time, the kinetic characteristics of mass adsorption can be determined, as shown in FIG. 9 for the dynamic detection of the growth of a single PPL layer. Initially, a baseline PWV was established with the sensor surface soaked in phosphate buffered saline (PBS) solution with pH=7.4. After 4 minutes, the PBS solution was replaced with PPL solution and stabilized for 10 min. Then the sensor surface was rinsed with PBS solution to remove any PPL that is not firmly attached to the sensor. The sensor produced a PWV shift of about 0.53 nm for PPL monolayer adsorption, and displayed lack of PWV drift over time periods up to one hour.

Figure 10:
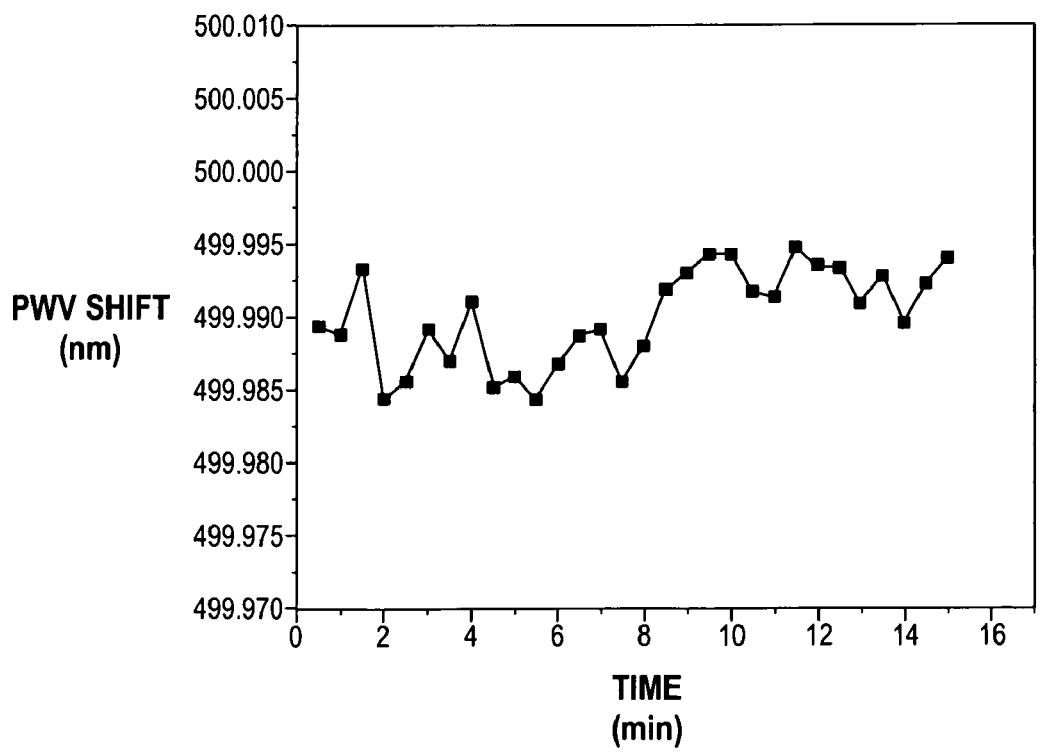
FIG. 10 is a plot of the time dependent PWV variation when the sensor was immersed in DI water and pumped at 10.2 µJ-mm$^{-2}$. Here, PWVs were calculated by fitting the recorded radiation spectra with a Lorentz distribution function.

The resolution at which small changes in laser output wavelength (pumped at 10.2 μJ-mm$^{-2}$) could be resolved was characterized by gathering, in rapid succession, many PWV measurements with the sensor surface exposed to DI water, and calculating the standard deviation of PWV determinations. The spectra were captured every 100 ms for a total time of 5 minutes. To determine the PWV with wavelength resolution that is better than the wavelength resolution between neighboring spectrometer pixels, the laser emission spectra were fitted using a standard Lorentzian distribution function. The PWV was determined by calculating the peak wavelength of the Lorentzian function. As shown in FIG. 10, the processed PWV vary in the range of 499.9843 nm to 499.9947 nm with a standard deviation (σ) of 3.26 pm. Assuming normal distribution, three times the standard deviation, 3σ, will be the minimum amount of shift to ensure accuracy of the next resolved PWV within 99.73% of total variation range. Therefore, system resolution was calculated as Δλ=3σ=9.78 pm.

Example 3

Figure 11:
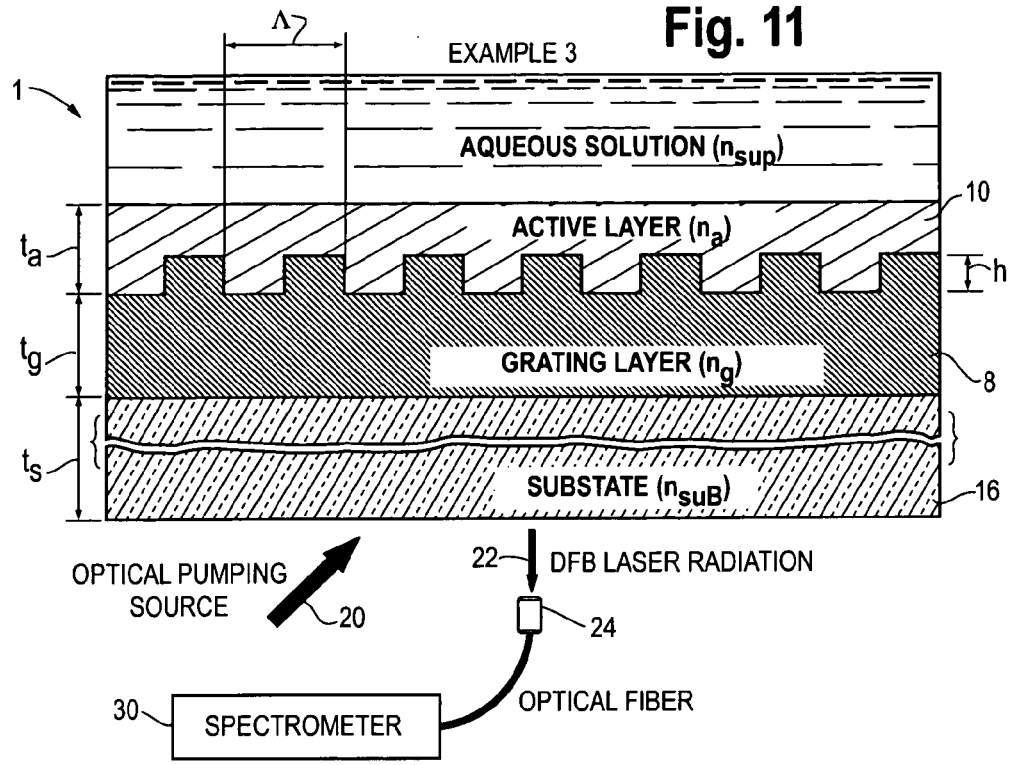
FIG. 11 is a cross-sectional diagram of a DFB laser sensor chip in accordance with another embodiment of the invention described below as Example 3.

FIG. 11 is a cross-section of a further example of a DFB laser sensor, including a substrate layer 16, periodic grating layer 8, and dye-doped active layer 10.

Either a glass, polyester, or polycarbonate material is used as a substrate layer 16 upon which the Bragg grating structure 8 is formed using either a Sol-gel porous $SiO_2$ or a UV curable polymer by a replica molding process. The active layer 10 may be spin-coated or evaporated onto the grating 8 surface. The potential dye materials for the active layer include: laser dye (e.g. Coumarin, Rhodamine, DCM, and LDS), doped polymers (such as Polymethyl-methacrylate (PMMA), SU-8, and epoxy), light emitting polymer (e.g. Poly-phenylene-vinylenes (PPV), Poly-phylene-ethynylenes (PPE), Polyfluorenes (PF) Ladder-type poly(p-phenylene) (LPPP), or quantum dot (e.g., ZnSe) doped dielectric materials. Typical dimensions are: Substrate 16 thickness $t_s$~1 mm, grating layer 8 thickness $t_g$~1 μm, and active layer 10 thickness $t_a$~0.5 μm. Typical refractive index are: Grating layer $n_g$~1.47, active layer index $n_a$~1.51. The following relation between index of refractions: $n_a$>$n_g$, $n_{sub}$, is necessary for light mode confinement.

Example 4

Figure 12:
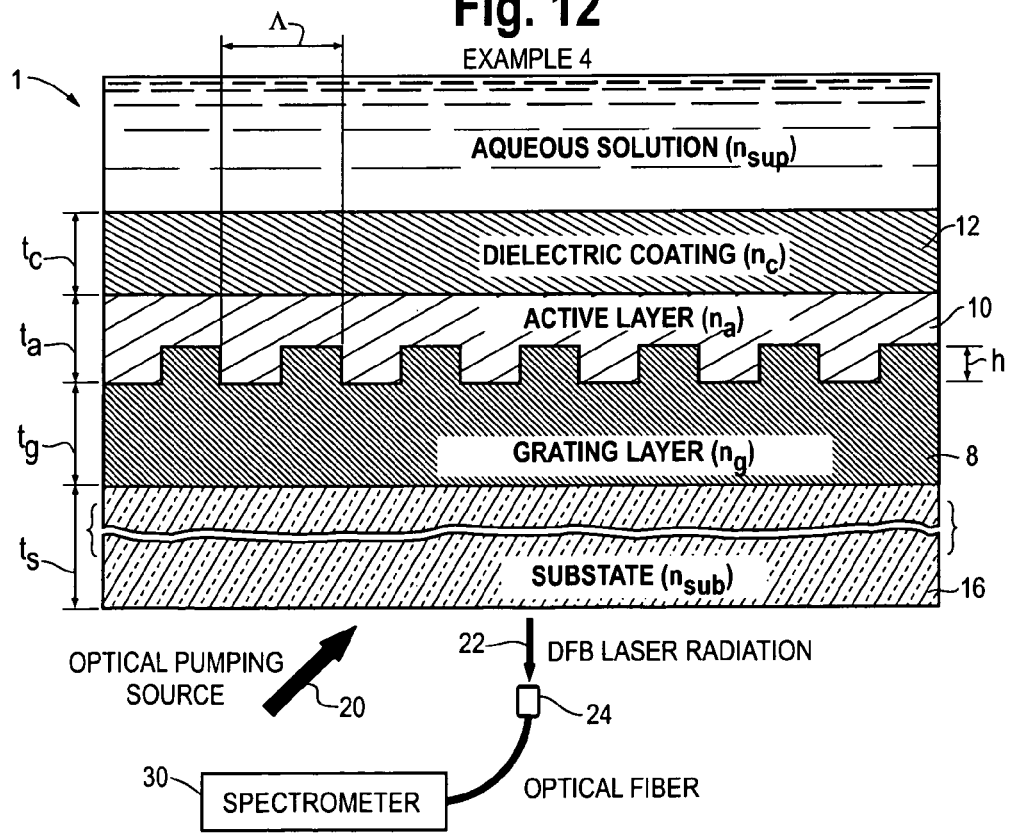
FIG. 12 is a cross sectional diagram of a DFB laser sensor chip described below as Example 4. Compared to Example 3, a high refractive index dielectric, such as titanium dioxide, hafnium dioxide, or tantalum oxide film is coated on top of the active layer to improve the sensor sensitivity, to reduce the radiation linewidth, and to lower the lasing threshold.

FIG. 12 is a cross-sectional diagram of a DFB laser sensor 1 in accordance with Example 4. Compared to Example 3, a high refractive index dielectric layer 12, such as titanium dioxide, hafnium dioxide, or tantalum oxide film, is coated on top of the active layer to improve the sensor sensitivity, to reduce radiation linewidth, and to lower the lasing threshold.

Example 5

Figure 13:
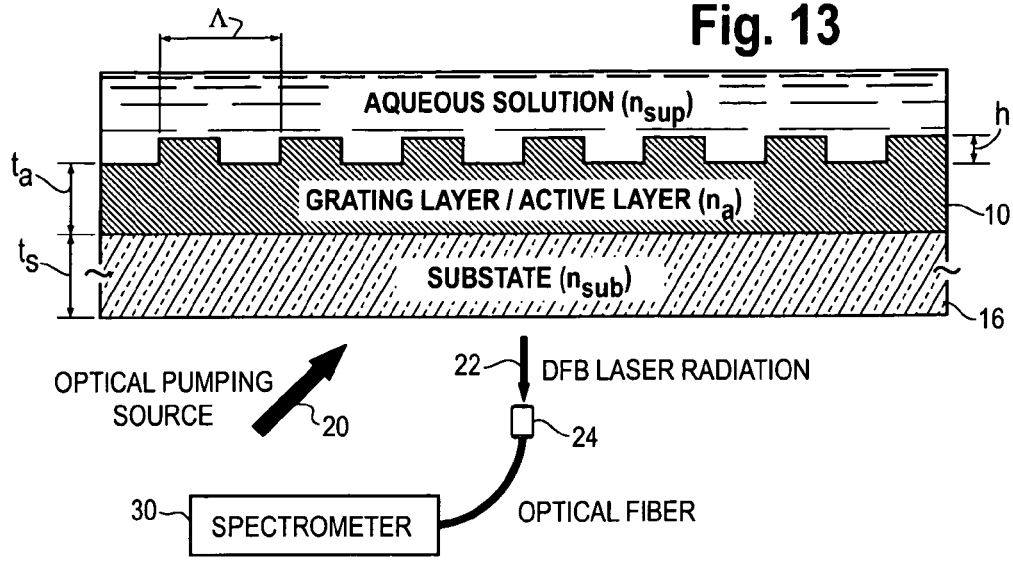
FIG. 13 is a cross-sectional diagram of a DFB laser sensor chip described below as Example 5. The grating layer and active layer are combined into a single layer. The surface of active layer was directly patterned to support Bragg diffraction grating. All previously-mentioned active materials, such as laser dye doped polymer, light emitting polymer, or quantum dot doped dielectric, could be used in this embodiment. The advantage of this structure would be simpler fabrication compared to Examples 3.

FIG. 13 is a cross sectional diagram of a DFB laser sensor 1 in accordance with yet another alternative embodiment. The grating layer and active layer of the previous embodiments are combined into a single active layer 10 containing a material which lases when pumped by the source 20 at an intensity above a threshold level. Examples of the active material in the layer 10 are laser dye (e.g. Coumarin, Rhodamine, DCM, and LDS), doped polymers (such as Polymethyl-methacrylate (PMMA), SU-8, and epoxy), light emitting polymer (e.g. Poly-phenylene-vinylenes (PPV), Poly-phylene-ethynylenes (PPE), Polyfluorenes (PF) Ladder-type poly(p-phenylene) (LPPP), or quantum dot (e.g., ZnSe) doped dielectric materials. The surface of active layer 10 is directly patterned to support Bragg diffraction grating.

The advantage of the structure of Example 5 would be simpler fabrication compared to the previous embodiments. The fabrication of the combined grating and active layer 10 would be in accordance with the replica molding methods described previously and in the previously cited patent literature.

Example 6

Figure 14:
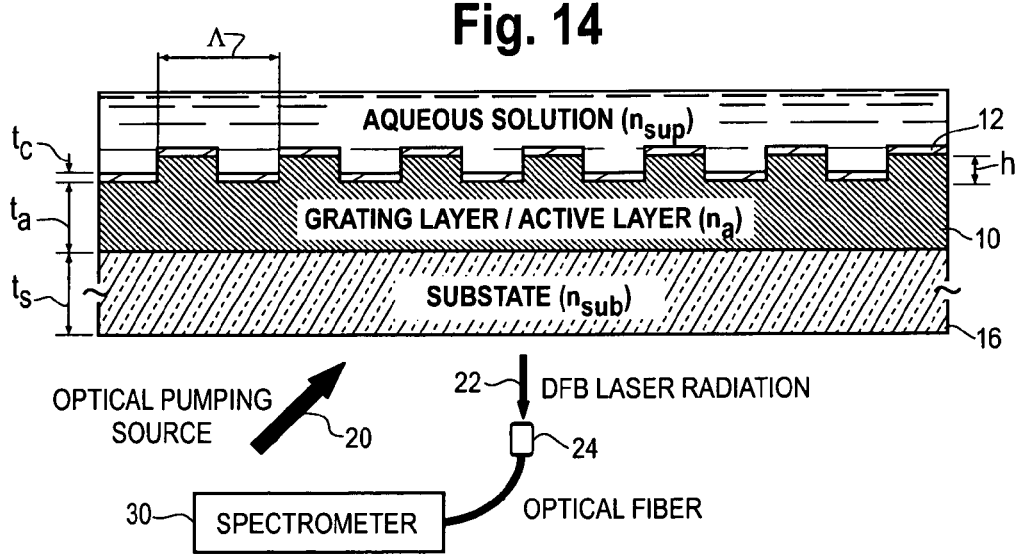
FIG. 14 is a cross-sectional diagram of a DFB laser sensor chip described below as Example 6. Compared to the Example 5, a high refractive index dielectric film, such as a titanium dioxide, hafnium dioxide, or tantalum oxide film, is coated on top of active/grating layer to improve the sensor sensitivity.

A further example of a DFB laser sensor 1 in accordance with Example 6 is shown in cross-section in FIG. 14. As compared to the Example 5 (FIG. 13), a high refractive index dielectric layer or film 12, such as titanium dioxide, hafnium dioxide, or tantalum oxide, is coated on top of active/grating layer 10 to improve the sensor sensitivity and raise the resonance mode closer to the sensor's upper surface.

Example 7

Inorganic Materials for Biosensor Active Layer

The active layer of the previously-described DFB laser biosensors are composed of organic materials, such as an active layer in the form of a laser dye doped PMMA film. However, in another example of how the invention can be practices, the active layer of the optically pumped DFB laser biosensor can also be made using inorganic materials.

Figure 15:
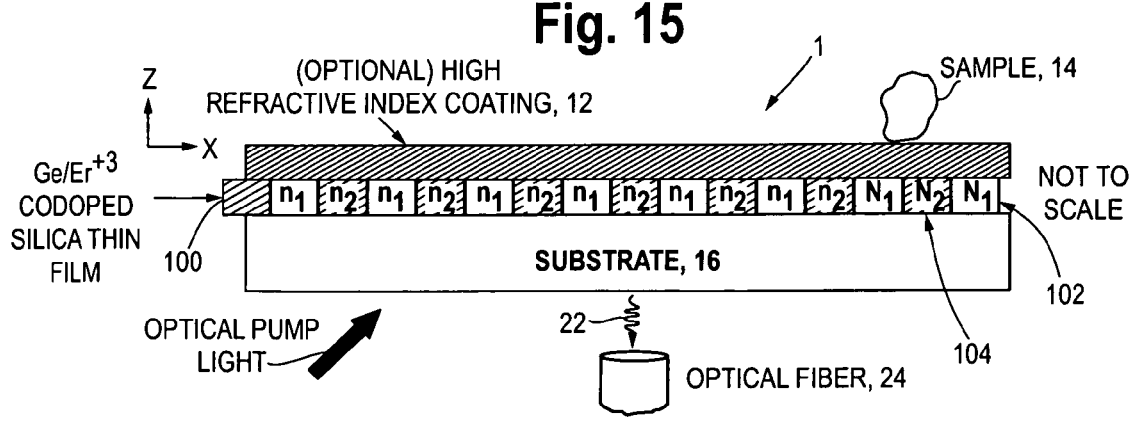
FIG. 15 is a cross-sectional diagram of an inorganic DFB laser sensor chip described below as Example 7.

FIG. 15 is a cross-sectional view of an inorganic DFB biosensor based on inorganic gain or active layer. The biosensor 1 includes a substrate 16 (which may be an organic or inorganic material such as glass or polycarbonate), and an inorganic active layer in the form of a Germanium-doped silica thin film 100 placed on the substrate 16. The Germanium doped silica thin film 100 is co-doped with rare earth ions so as to produce a luminescent response having an output wavelength 22 when pumped from an external optical source. The Germanium doped silica thin film 100 is constructed with periodic alternating regions 102, 104, defined by variation in the index of refraction of such periodic alternating regions. These variations of index of refraction are indicated by the regions 102 with index of refraction n1, and regions 104 with index of refraction n2. While a one dimensional periodic variation is shown, it will be appreciated that the structure extends in the Y direction. Various two-dimensional structures are possible, such as an array of posts or holes in a rectangular or hexagonal grid. Additionally, the 1-dimensional variations may have different geometrical forms, duty cycle, etc. Output light 22 from the sensor 1 is captured by an optical fiber at near normal incidence and supplied to a spectrometer for determination of a shift in the PWV of the sensor due to the presence of the sample 14.

Figure 17:
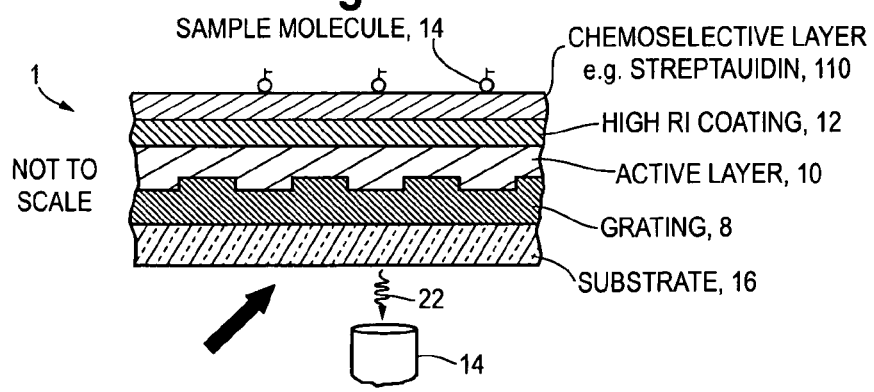
FIG. 17 is an illustration of a biosensor which, during use, a chemoselective layer is initially applied to the surface of the biosensor and then a sample containing a target molecule or substance is applied to the chemoselective layer and selectively bound to the surface of the biosensor.

An optional, relatively high refractive index material 12 is shown deposited on the inorganic active layer 100. A sample 14 is placed on the high index coating 12. The sample 14 may include an initial chemoselective medium (e.g., streptavidin) and a further sample molecule (e.g., biotin, DNA sample, etc). which is selectively bound to the chemoselective layer, as shown in FIG. 17 and described subsequently.

The inorganic DFB laser biosensor has several advantages compared to its organic counterpart. Firstly, inorganic material exhibits better thermal stability, which helps to reduce the variation in the lasing wavelength (output wavelength in the resonant mode). The small emission wavelength variation exhibit by the inorganic DFB laser biosensor improves the wavelength resolution of the overall biosensor system. Secondly, it is possible to control the material refractive index (RI) contrast, $\Delta n = n_2 - n_1$ in spatially separated, periodic areas of the biosensor surface. The magnitude of the RI contrast between relatively high and relatively low indices of refraction can be made very small, and as low as $10^{-5}$ to $10^{-2}$. See K. O. Hill and G. Meltz, Journal of Lightwave Technology 15, 1263-1276 (1997), incorporated by reference herein. Smaller RI contrast results in an even higher cavity Q-factor, i.e. narrower emission linewidth. According to numerical simulation (RCWA) results for a biosensor as shown in FIG. 15, the resonance mode of the inorganic biosensor exhibits a Q-factor around $10^6$ when $\Delta n$ is as small as $10^{-3}$. Moreover, it has been numerically demonstrated that the decrease of $\Delta n$ does not affect the dynamic range of the DFB laser sensor.

The photo-induced RI change in Germania (Ge)-doped silica has been studied and used to produce fiber Bragg grating. Two techniques have been demonstrated to define sub-wavelength refractive index (RI) variation in Ge-doped silica fiber: two beams interference photolithography and direct photolithography using a pre-designed phase mask. These techniques are described in D. S. Starodubov, V. Grubsky, and J. Feinberg, Electronics Letters 33, 1331-1333 (1997) and in D. S. Starodubov, V. Grubsky, J. Feinberg, B. Kobrin, and S. Juma, Optics Letters 22, 1086-1088 (1997), the contents of both of which are incorporated by reference herein. The methods described in the above publications can be extended to introduce RI variation in a Ge-doped silica thin film shown in FIG. 15.

Rare earth ions (e.g., $Er^{+3}$ or $Yb^{+3}$) are usually used to dope inorganic thin films or fiber to achieve photoluminescence in response to optical pumping. See V. Toccafondo, A. Cerqueira, S. Faralli, E. Sani, A. Toncelli, M. Tonelli, and F. Di Pasquale, Journal of Applied Physics 101,—(2007); L. Yang, T. Carmon, B. Min, S. M. Spillane, and K. J. Vahala, Applied Physics Letters 86,—(2005) and X. J. Wang and M. K. Lei, Thin Solid Films 476, 41-45 (2005), the content of which is incorporated by reference herein. Thus, in preparation of the thin inorganic film shown in FIG. 15, rare earth ions are introduced into Germaniam-doped silica material to provide a luminescent substance in the subsequently formed film.

Compared to organic laser dye (Coumarin and Rhodamine) doped PMMA film, the $Er^{+3}$ doped silica shows long photon lifetime (on the order of 10 ms). The photon lifetime of Rhodamine-6G dye is only 3.3 ns. Therefore, it is possible to optically pump the fabricated inorganic DFB laser with a continuous wave (CW) diode laser, or a microsecond flash lamp.

Example 8

In another example, the structure of FIG. 15 can be used, but instead of an inorganic thin film active layer 100, the thin film active layer 100 is made of an organic material. Thus, with reference to FIG. 15, the biosensor includes a substrate 16, a thin film active layer 100 applied to the substrate, wherein the thin film active layer comprises a periodically alternating regions in the thin film of relatively high and relatively low index of refraction, as indicated at 102 and 104. The thin film active layer contains an active substance which emits narrow-band light when pumped with radiation above a threshold intensity level from an external optical source. The active layer of the biosensor exhibits a high Q-factor optical resonance mode in the thin film active layer.

The substance in the active layer could take several possible forms such as a laser dye (e.g. Coumarin, Rhodamine, DCM, and LDS), a doped polymer (such as Polymethyl-methacrylate (PMMA), SU-8, and epoxy), a light emitting polymer (e.g. Poly-phenylene-vinylenes (PPV), Poly-phylene-ethynylenes (PPE), Polyfluorenes (PF) Ladder-type poly (p-phenylene) (LPPP), or a quantum dot (e.g., CdSe, CdS, ZnSe, and core/shell composite quantum dots).

Additional Examples

Figure 16A:
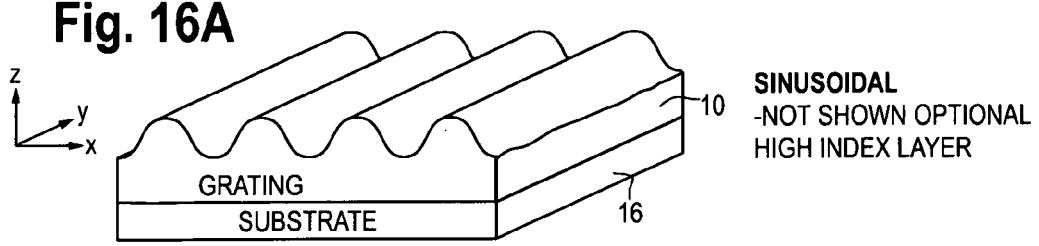
FIGS. 16A-16D are perspective views, partially in cross-section, of different types of one dimensional gratings which can used for the DFB laser sensor.
Figure 16B:
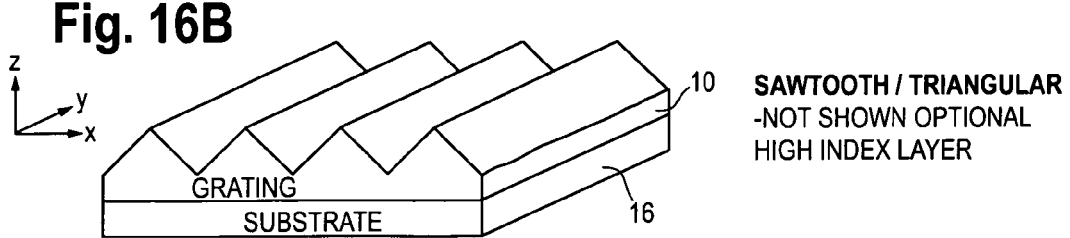
Figure 16C:
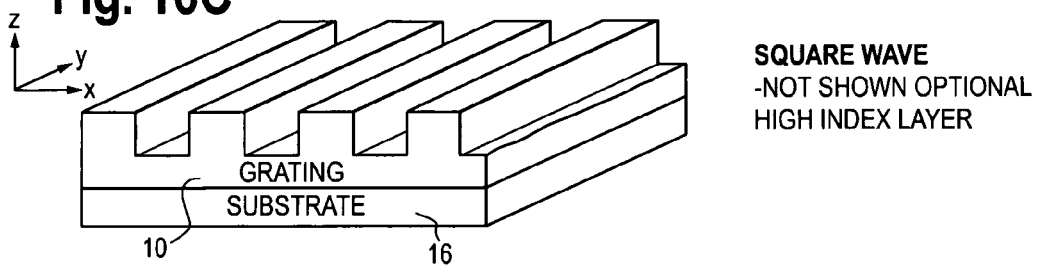
Figure 16D:
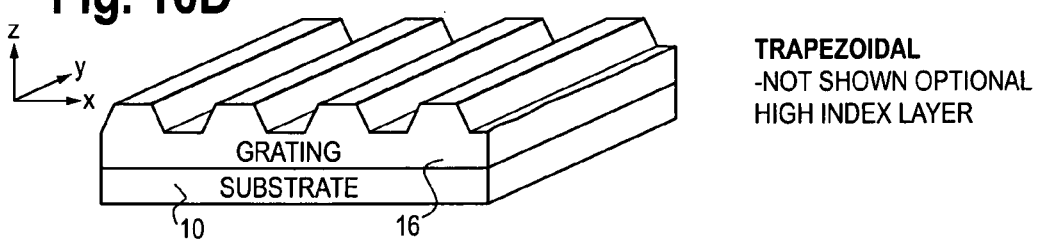

1-D Gratings
FIGS. 16A-16D show several possible configurations of the one-dimensional periodic surface gratings described in several previous embodiments. In FIG. 16A, the grating is in the form of a sinusoidal pattern of alternating high and low regions which extends periodically in the X direction and longitudinally in the Y direction. FIG. 16B shows a saw-tooth or triangular grating pattern. FIG. 16C shows a square wave grating pattern. FIG. 16D shows a trapezoidal grating pattern. All of the above patterns can be made using replica molding techniques described above and in the previously-cited patent literature.

An optional high index of refraction layer can be deposited on the top of the grating layer (or on top of an active layer which is deposited on the gratings shown in FIGS. 16A-16D).

2-D Gratings

In any of the above embodiments, the periodic surface grating can take the form of a two-dimensional (2-D) grating structure. The 2-D grating structure can take any one of several possible configurations, such as a two-dimensional array of posts; a two-dimensional array of holes; an array of holes or posts arranged in a rectangular grid; and an array of holes or posts arranged in a hexagonal grid.

Thus, in one example a biosensor is provided comprising a substrate, a periodic surface grating layer applied to the substrate, wherein the periodic surface grating layer comprises an active layer containing a substance which emits narrow-band light and exhibiting a high Q-factor optical resonance mode when pumped with radiation above a threshold intensity level from an external source. The periodic surface grating is in the form of a two-dimensional periodic surface grating which comprises one of the following configurations: a two-dimensional array of posts; a two-dimensional array of holes; an array of holes or posts arranged in a rectangular grid; and an array of holes or posts arranged in a hexagonal grid.

As another example, a biosensor is configured to have a substrate, a periodic surface grating layer applied to the substrate, and an active layer applied to the periodic surface grating layer, wherein the active layer-contains a substance which emits narrow-band light and which exhibits a high Q-factor optical resonance mode when pumped with radiation above a threshold intensity level from an external source. The periodic surface grating is in the form of a two-dimensional periodic surface grating which comprises one of the following configurations: a two-dimensional array of posts; a two-dimensional array of holes; an array of holes or posts arranged in a rectangular grid; and an array of holes or posts arranged in a hexagonal grid.

A high index of refraction coating can be applied to the grating in the 2-D embodiments, as well as in the example of 1-D gratings.

Integration of Biosensor with Sample Handling Devices

The biosensors of this disclosure can be physically incorporated into any suitable and convenient larger scale sample handling structure for containing a sample to be tested by the biosensor. For example, the biosensor can be affixed to the bottom of the microplate (e.g., with 12, 24, 96, 384, 1536 or other number of individual sample wells). The biosensor can also be integrated with out structures, such as a microscope slide, a chip or device having microfluidic fluid channels, a test tube, a petri dish, a flask, a tape cassette and a cover slip.

Devices for Detecting Shift in Output Wavelength of Biosensor

The device for detecting the shift in the output wavelength of the biosensor due to the presence of the sample on the sensor surface (spectrometer device 30 in FIG. 6 and other figures) can take a variety of forms. Various types of spectrometers, including imaging spectrometers, are possible. Other spectrographic devices may be used, including a monochromater, an interferometer, and a graded wavelength filter wavelength detection apparatus, see Ganesh et al., Compact wavelength detection system incorporating guided-mode resonance filter, Applied Physics Letters 90, 081103 (2007), the content of which is incorporated by reference herein. Another possibility is position-sensitive detector for wavelength determination, see U.S. Pat. No. 7,310,153 and Kiesel et al., Compact, low-cost, and high resolution interrogation unit for optical sensors, Applied Physics Letters 89, 201113 (2006), the content of both of which are incorporated by reference herein.

Methods for Testing a Sample.

In view of the above description, it will be appreciated that we have described a method of testing a sample. The sample can take any form, including small molecule, drug, protein, virus, DNA, etc. The method includes the steps of: depositing the sample (14 in FIG. 1) on a biosensor comprising a substrate, a periodic surface grating layer applied to the substrate, wherein the periodic surface grating comprises an active layer 10 (as described in Examples 5 and 6); pumping the active layer 10 with an external light source (20, FIGS. 13, 14) at an intensity level above a threshold to produce a high Q-factor optical resonance made in the grating layer; collecting radiation 22 from the sensor and directing the radiation to a spectrometer (30); and determining a shift in the peak wavelength value of the radiation due to the presence of the sample.

In another aspect, a method of testing a sample is disclosed comprising the steps of depositing the sample on a biosensor comprising a substrate, a periodic surface grating layer applied to the substrate, and an active layer applied to the periodic surface grating layer (biosensor according to Examples 1-4); pumping the active layer with an external light source (20) at an intensity level above a threshold to produce a high Q-factor optical resonance mode in the active layer 10; collecting radiation 22 from the sensor and directing the radiation to a spectrometer 30; and determining a shift in the peak wavelength value of the radiation due to the presence of the sample.

In another variation, a method of testing a sample has been described of providing a biosensor comprising a substrate, and a thin film active layer applied to the substrate, wherein the thin film active layer comprises periodically alternating regions in the thin film of relatively high and relatively low index of refraction (see examples 7 and 8 and FIG. 15), and wherein the thin film active layer contains an active substance which emits narrow-band light when pumped with radiation above a threshold intensity level from an external source (e.g., laser dye in an organic active layer embodiment or rare earth ions in an inorganic active layer embodiment), depositing a sample on the surface of the biosensor; pumping the active layer with an external light source at an intensity level above a threshold to produce a high Q-factor optical resonance mode in the thin film active layer; collecting radiation from the sensor and directing the radiation to a spectrometer or spectrometer-like device capable of detecting a shift in the output wavelength of the biosensor; and determining a shift in the peak wavelength value of the radiation due to the presence of the sample.

As shown in FIG. 17, in many embodiments, the methods may include a step of applying a chemoselective layer 110 to the sensor surface and then applying the sample 14 to the chemoselective layer. For example, the chemoselective layer 110 may be a streptavidin solution and the sample molecules 14 may comprise a protein, DNA fragment, etc. which is selectively bound to the chemoselective layer 110. While the embodiment of FIG. 17 shows a grating layer 8 and an active layer 10 deposited on the grating layer (as in Examples 1-4), the technique of using the chemoselective layer 110 and the sample molecules 14 applied to the chemoselective layer can of course be used in the other embodiments such as Examples 5, 6, 7 and 8.

The samples which can be tested/measured with the biosensors of this disclosure can vary widely. Examples include molecules having a molecular weight of less than 1000 daltons, molecules with a molecular weight of between 1000 and 10,000 daltons, blood, serum, spinal fluid, environmental water samples, amino acids, proteins, nucleic acids, bacteria, lipids, carbohydrates, nucleic acid polymers, viral particles, viral components, cellular components, extracts of viral or cellular components, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples.

What is claimed is:

1. A biosensor comprising:
   a substrate, and a periodic surface grating layer applied to the substrate, wherein the periodic surface grating layer comprises an active layer containing a substance which emits narrow-band light and exhibiting a high Q-factor optical resonance mode when pumped with radiation above a threshold intensity level from an external source; wherein the substance in the active layer is selected from the group of substances consisting of a laser dye, a doped polymer, a light emitting polymer and a quantum dot; and
   wherein the biosensor is incorporated into a sample handling structure for containing a sample to be tested by the biosensor.

2. The biosensor of claim 1, further comprises a high index of refraction material coated onto the periodic surface grating.

3. The biosensor of claim 1, wherein the grating layer has an index of refraction which is greater than the index of refraction of the substrate layer.

4. The biosensor of claim 1, wherein the periodic surface grating comprises a one-dimensional periodic surface grating.

5. The biosensor of claim 1, wherein the periodic surface grating comprises a two-dimensional periodic surface grating.

6. The biosensor of claim 5, wherein the two-dimensional periodic surface grating comprises one of the following configurations: a two-dimensional array of posts; a two-dimensional array of holes; an array of holes or posts arranged in a rectangular grid; and an array of holes or posts arranged in a hexagonal grid.

7. The biosensor of claim 1, wherein the periodic surface grating comprises one of the following configurations: a 1-dimensional sinusoidal profile; a 1-dimensional triangular profile; a 1-dimensional square wave profile; and a 1-dimensional trapezoidal profile.

8. The biosensor of claim 1, wherein the sample handling structure is selected from the group of structures consisting of a microplate with individual sample wells, a microscope slide, a chip or device having microfluidic fluid channels, a test tube, a petri dish, a flask, a tape cassette and a cover slip.

9. A biosensor comprising:
   a substrate, a periodic surface grating layer applied to the substrate, and an active layer applied to the periodic surface grating layer, wherein the active layer contains a substance which emits narrow-band light and which exhibits a high Q-factor optical resonance mode when pumped with radiation above a threshold intensity level from an external source, wherein the substance in the active layer is selected from the group of substances consisting of a laser dye, a doped polymer, a light emitting polymer and a quantum dot; and
   wherein the biosensor is incorporated into a sample handling structure for containing a sample to be tested by the biosensor.

10. The biosensor of claim 9, further comprises a high index of refraction material coated onto the active layer.

11. The biosensor of claim 9, wherein the active layer has an index of refraction which is greater than the index of refraction of the grating layer.

12. The biosensor of claim 9, wherein the periodic surface grating comprises a one-dimensional periodic surface grating.

13. The biosensor of claim 9, wherein the periodic surface grating comprises a two-dimensional periodic surface grating.

14. The biosensor of claim 13, wherein the two-dimensional periodic surface grating comprises one of the following configurations: a two-dimensional array of posts; a two-dimensional array of holes; an array of holes or posts arranged in a rectangular grid; and an array of holes or posts arranged in a hexagonal grid.

15. The biosensor of claim 9, wherein the periodic surface grating comprises one of the following configurations: a 1-dimensional sinusoidal profile; a 1-dimensional triangular profile; a 1-dimensional square wave profile; and a 1-dimensional trapezoidal profile.

16. A biosensor comprising:
   a substrate;
   an inorganic active layer in the form of a Germanium doped silica thin film placed on the substrate, the Germanium doped silica thin film co-doped with rare earth ions so as to produce a luminescent response having an output wavelength and exhibit a high Q-factor optical resonance mode when pumped with radiation from an external optical source;
   wherein the Germanium doped silica thin film is constructed with periodic alternating regions defined by variation in the index of refraction of such periodic alternating regions.

17. The biosensor of claim 16, wherein the periodic alternating regions comprise alternating regions having a refractive index of n1 and n2, and wherein $\Delta n = n2 - n1$ is between $10^{-5}$ and $10^{-2}$.

18. The biosensor of claim 16, further comprising a relatively high refractive index material deposited on the inorganic active layer.

19. The biosensor of claim 16, wherein the biosensor is incorporated into a sample handling structure for containing a sample to be tested by the biosensor.

20. A biosensor comprising:
   a substrate,
   a thin film active layer applied to the substrate, wherein the thin film active layer comprises a periodically alternating regions in the thin film of relatively high and relatively low index of refraction,
   and wherein the thin film active layer contains an active substance which emits narrow-band light when pumped with radiation above a threshold intensity level from an external optical source and exhibiting a high Q-factor optical resonance mode in the thin film active layer, wherein the active substance in the thin film active layer is selected from the group of substances consisting of a laser dye, a doped polymer, a light emitting polymer and a quantum dot.

21. The biosensor of claim 20 wherein the biosensor is incorporated into a sample handling structure for containing a sample to be tested by the biosensor.

22. A system for testing a sample, comprising:
an optical pump;
a biosensor comprising a substrate, and a periodic surface grating layer applied to the substrate, wherein the periodic surface grating layer comprises an active layer containing a substance which emits narrow-band light and exhibiting a high Q-factor optical resonance mode when pumped with radiation above a threshold intensity level from the optical pump, wherein the substance in the active layer is selected from the group of substances consisting of a laser dye, a doped polymer, a light emitting polymer and a quantum dot; and
a device capable of detecting a shift in the wavelength of the narrow band light emitted by the biosensor.

23. The system of claim 22, wherein the optical pump is selected from the group consisting of a flash lamp, a pulsed laser and a continuous wave (CW) diode laser.

24. The system of claim 22, wherein the device capable of detecting a shift in the output wavelength of the biosensor is selected from the group of devices consisting of a spectrometer, a monochrometer, an interferometer, a graded wavelength filter wavelength detection apparatus, and a position-sensitive detector for wavelength determination.

25. A system for testing a sample, comprising:
an optical pump;
a biosensor comprising a substrate, a periodic surface grating layer applied to the substrate, an active layer applied to the periodic surface grating layer, wherein the active layer contains a substance which emits narrow-band light and which exhibits a high Q-factor optical resonance mode when pumped with radiation above a threshold intensity level from the optical pump, wherein the substance in the active layer is selected from the group of substances consisting of a laser dye, a doped polymer, a light emitting polymer and a quantum dot; and
a device capable of detecting a shift in the wavelength of the narrow band light emitted by the biosensor.

26. The system of claim 25, wherein the optical pump is selected from the group consisting of a flash lamp, a pulsed laser and a continuous wave (CW) diode laser.

27. The system of claim 25, wherein the device capable of detecting a shift in the output wavelength of the biosensor is selected from the group of devices consisting of a spectrometer, a monochrometer, an interferometer, a graded wavelength filter wavelength detection apparatus, and a position-sensitive detector for wavelength determination.

28. A system for testing a sample, comprising:
an optical pump;
a biosensor comprising a substrate, a thin film active layer applied to the substrate, wherein the thin film active layer comprises a periodically alternating regions in the thin film of relatively high and relatively low index of refraction, wherein the thin film active layer contains an active substance which emits narrow-band light when pumped with radiation above a threshold intensity level from the optical pump and exhibiting a high Q-factor optical resonance mode in the thin film active layer, wherein the active substance in the thin film active layer is selected from the group of substances consisting of a laser dye, a doped polymer, a light emitting polymer and a quantum dot;
a device capable of detecting a shift in the wavelength of the narrow-band light; and
wherein the optical pump is selected from the group consisting of a flash lamp and a continuous wave (CW) diode laser.

29. The system of claim 28, wherein the device capable of detecting a shift in the output wavelength of the biosensor is selected from the group of devices consisting of a spectrometer, a monochrometer, an interferometer, a graded wavelength filter wavelength detection apparatus, and a position-sensitive detector for wavelength determination.

30. A method of testing a sample, comprising the steps of:
depositing the sample on a biosensor comprising a substrate, a periodic surface grating layer applied to the substrate, wherein the periodic surface grating comprises an active layer, wherein the active layer includes an active substance which emits narrow-band light when pumped with radiation above a threshold intensity level from an optical pump and exhibiting a high Q-factor optical resonance mode, the active substance selected from the group of substances consisting of a laser dye, a doped polymer, a light emitting polymer and a quantum dot;
pumping the active layer with an external light source at an intensity level above a threshold to produce a high Q-factor optical resonance mode in the grating layer having an output wavelength;
collecting radiation from the sensor and directing the radiation to a spectrometer or spectrometer-like device capable of detecting a shift in the output wavelength of the biosensor; and
determining a shift in the peak wavelength value of the radiation due to the presence of the sample.

31. The method as claimed in claim 30, wherein the method further comprises the step of applying a chemoselective layer to the surface of the biosensor prior to the step of applying the sample to the biosensor, wherein the chemoselective layer is used to selectively bind the sample to the biosensor.

32. The method as claimed in claim 30, wherein the sample is selected from the group of samples consisting of molecules having a molecular weight of less than 1000 daltons, molecules with a molecular weight of between 1000 and 10,000 daltons, blood, serum, spinal fluid, environmental water sample, amino acids, proteins, nucleic acids, bacteria, lipids, carbohydrates, nucleic acid polymers, viral particles, viral components, cellular components, and extracts of viral or cellular components, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples.

33. A method of testing a sample, comprising the steps of:
depositing the sample on a biosensor comprising a substrate, a periodic surface grating layer applied to the substrate, and an active layer applied to the periodic surface grating layer, wherein the active layer includes an active substance which emits narrow-band light when pumped with radiation above a threshold intensity level from an optical pump and exhibiting a high Q-factor optical resonance mode, the active substance selected from the group of substances consisting of a laser dye, a doped polymer, a light emitting polymer and a quantum dot;

pumping the active layer with an external light source at an intensity level above a threshold to produce a high Q-factor optical resonance mode in the active layer having an output wavelength;

collecting radiation from the sensor and directing the radiation to a spectrometer or spectrometer-like device capable of detecting a shift in the output wavelength of the biosensor; and determining a shift in the peak wavelength value of the radiation due to the presence of the sample.

34. The method as claimed in claim 33, wherein the method further comprises the step of applying a chemoselective layer to the surface of the biosensor prior to the step of applying the sample to the biosensor, wherein the chemoselective layer is used to selectively bind the sample to the biosensor.

35. The method as claimed in claim 33, wherein the sample is selected from the group of samples consisting of molecules having a molecular weight of less than 1000 daltons, molecules with a molecular weight of between 1000 and 10,000 daltons, blood, serum, spinal fluid, environmental water sample, amino acids, proteins, nucleic acids, bacteria, lipids, carbohydrates, nucleic acid polymers, viral particles, viral components, cellular components, and extracts of viral or cellular components, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples.

36. A method of testing a sample, comprising the steps of:
providing a biosensor comprising a substrate, and a thin film active layer applied to the substrate, wherein the thin film active layer comprises periodically alternating regions in the thin film of relatively high and relatively low index of refraction, and wherein the thin film active layer contains an active substance which emits narrow-band light when pumped with radiation above a threshold intensity level from an external source, wherein the active substance is selected from the group of substances consisting of a laser dye, a doped polymer, a light emitting polymer and a quantum dot, depositing a sample on the surface of the biosensor;

pumping the active layer with an external light source at an intensity level above a threshold to produce a high Q-factor optical resonance mode in the thin film active layer;

collecting radiation from the sensor and directing the radiation to a spectrometer or spectrometer-like device capable of detecting a shift in the output wavelength of the biosensor; and determining a shift in the peak wavelength value of the radiation due to the presence of the sample.

37. The method as claimed in claim 36, wherein the method further comprises the step of applying a chemoselective layer to the surface of the biosensor prior to the step of applying the sample to the biosensor, wherein the chemoselective layer is used to selectively bind the sample to the biosensor.

38. The method as claimed in claim 36, wherein the sample is selected from the group of samples consisting of molecules having a molecular weight of less than 1000 daltons, molecules with a molecular weight of between 1000 and 10,000 daltons, blood, serum, spinal fluid, environmental water sample, amino acids, proteins, nucleic acids, bacteria, lipids, carbohydrates, nucleic acid polymers, viral particles, viral components, cellular components, and extracts of viral or cellular components, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples.

* * * * *